United States Patent
Yang

(10) Patent No.: US 7,160,702 B2
(45) Date of Patent: Jan. 9, 2007

(54) METHODS AND NUCLEIC ACID VECTORS FOR RAPID EXPRESSION AND SCREENING OF CDNA CLONES

(76) Inventor: Shuwei Yang, c/o GeneCopoeia, Inc. 15 Wormans Mill Ct., Suites D & E, Frederick, MD (US) 21701

( * ) Notice: Subject to any disclaimer, the term of this patent is extended or adjusted under 35 U.S.C. 154(b) by 207 days.

(21) Appl. No.: 10/627,711

(22) Filed: Jul. 28, 2003

(65) Prior Publication Data
US 2004/0115812 A1   Jun. 17, 2004

Related U.S. Application Data

(60) Provisional application No. 60/398,589, filed on Jul. 26, 2002.

(51) Int. Cl.
*C12N 15/66*   (2006.01)
(52) U.S. Cl. .................. 435/91.41; 435/91.52
(58) Field of Classification Search ............... None
See application file for complete search history.

(56) References Cited

U.S. PATENT DOCUMENTS

| | | |
|---|---|---|
| 4,673,640 A | 6/1987 | Backman |
| 4,959,317 A | 9/1990 | Sauer |
| 5,348,886 A | 9/1994 | Lee et al. |
| 5,783,386 A | 7/1998 | Jacobs, Jr. et al. |
| 6,143,557 A | 11/2000 | Hartley et al. |
| 6,410,317 B1 | 6/2002 | Farmer |

2003/0124555 A1   7/2003   Brasch et al.

FOREIGN PATENT DOCUMENTS

WO   WO 02/46372   6/2002

OTHER PUBLICATIONS

International Search Report dated Oct. 20, 2004.
Abremski et al., 1986, J. Biol. Chem. 261:391.
Araki et al., 1992, Biol. 225:25.
Campbell, 1992, J. Bacteriol. 174:7495.
Devine et al. (Nucl. Acids Res. 22:3765-3772 (1994).
Hasan et al. (1987, Gene 56:145-151).
Hoess et al., 1986, Nucleic Acids Research 14:2287.
Lucklow et al., J. Virol. 67:4566-4579 (1993).
Palazzolo et al., 1990, Gene 88:25-36.
Posfai et al. (1994, Nucl. Acids Res. 22:2392-2398).
Qian et al., 1992, J. Biol. Chem. 267:7794.
Schlake et al. (Biochemistry 33:12746-12751 (1994)).
Waterhouse et al. (Nucleic Acids Res. 21 (9):2265 (1993)).

*Primary Examiner*—James Ketter
(74) *Attorney, Agent, or Firm*—Kening Li

(57) ABSTRACT

Recombinant DNA vectors and methods for cloning and expressing nucleic acid molecules by using a combination of site-specific recombination and end-to-end joining or linking of nucleic acid molecules, such as endonuclease restriction digestion and ligation. The DNAs, vectors and methods can be used for inserting, exchanging, transferring a variety of DNA segment(s) both in vitro and in vivo. Also disclosed are linker molecules and methods using these linkers the can be used for cloning a gene of interest into an expression vector in one-step. The linker sequences comprise adapter sequences for cloning purposes, as well as eukaryotic and prokaryotic ribosome binding sites for increase translation efficiency.

24 Claims, 28 Drawing Sheets

Product      Byproduct    Fig. 10

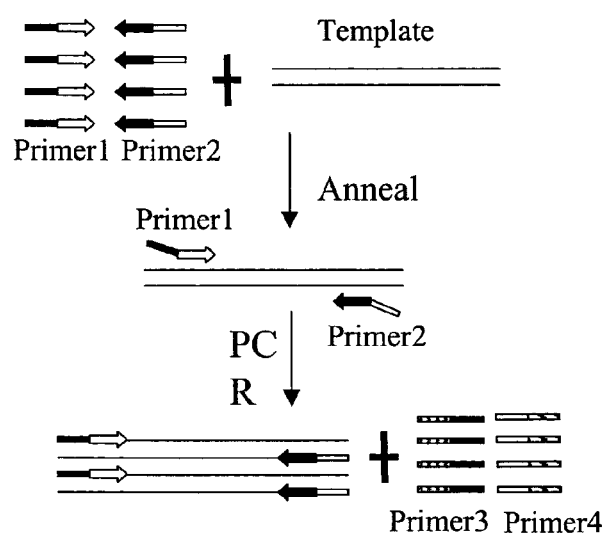
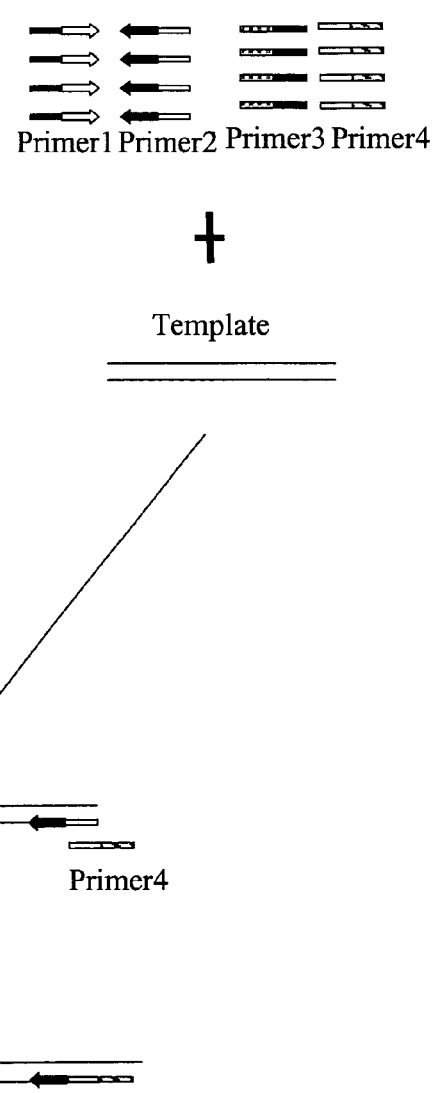
Fig.18

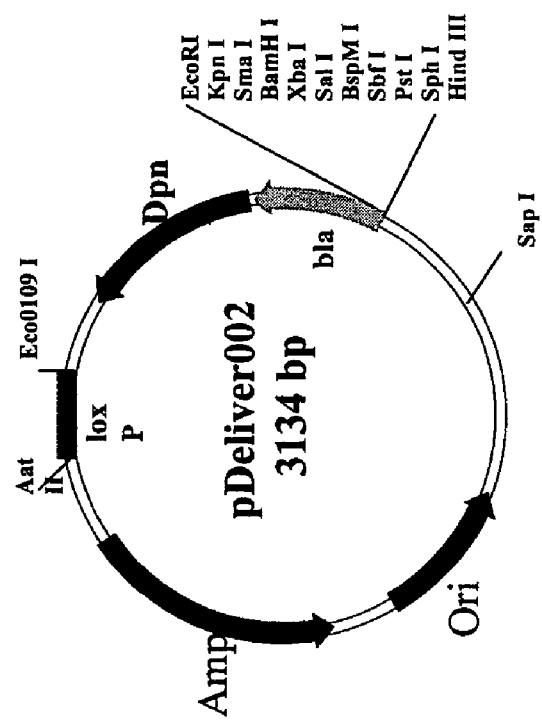
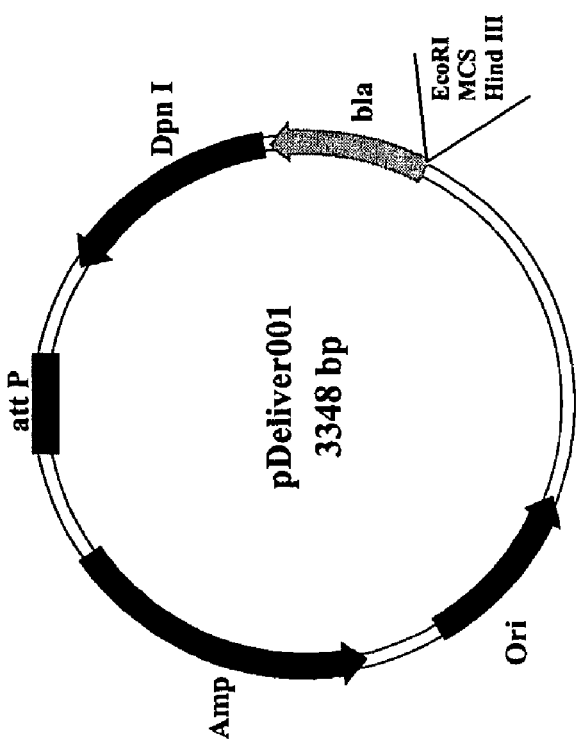
Fig.19

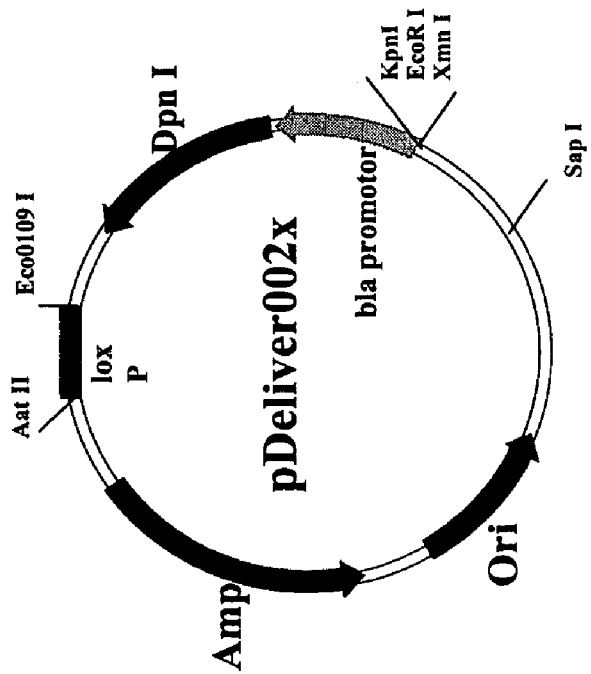
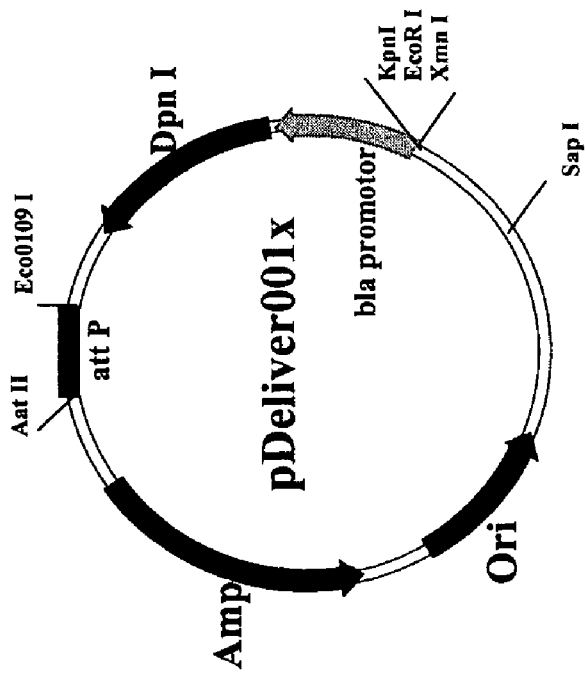
Fig. 20

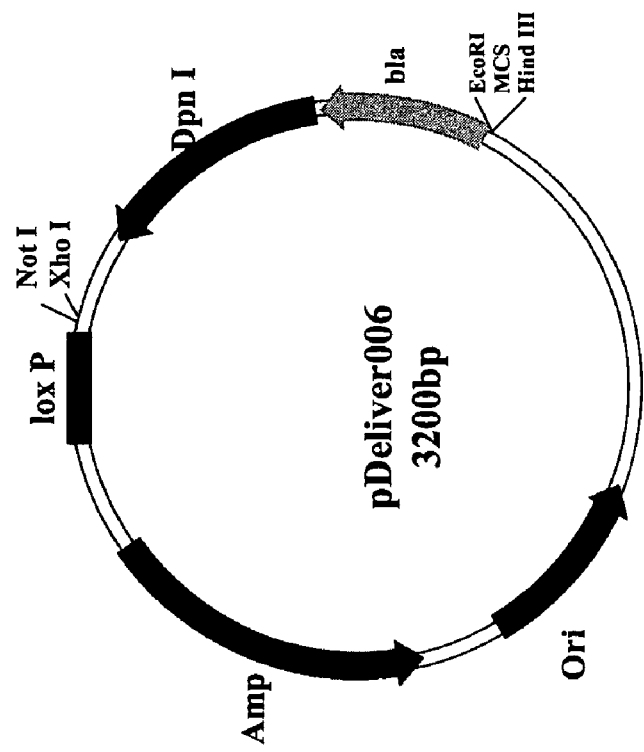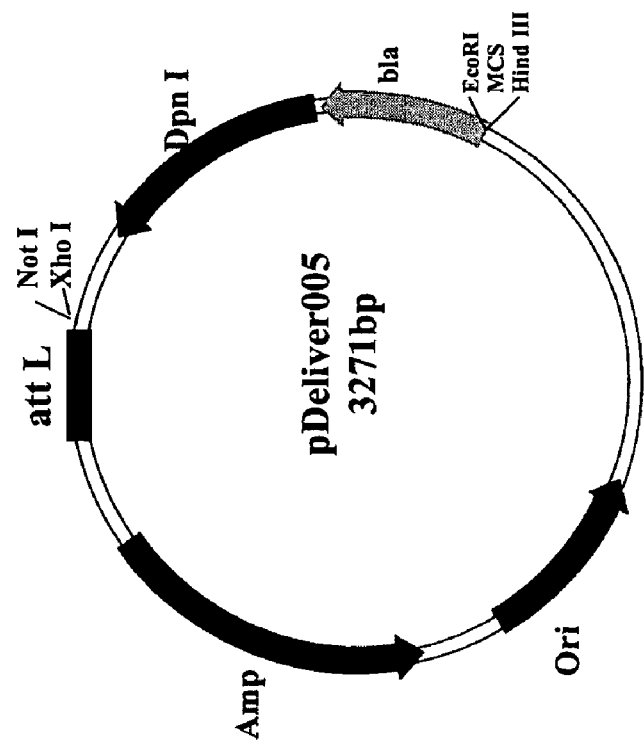
Fig. 21

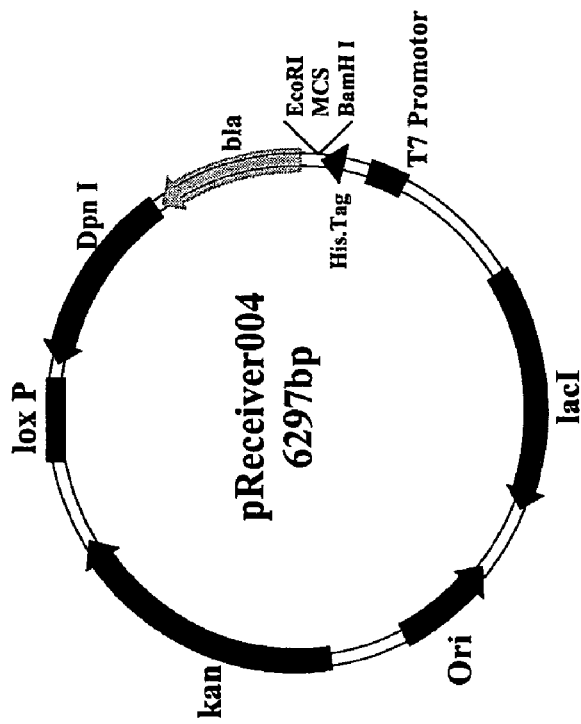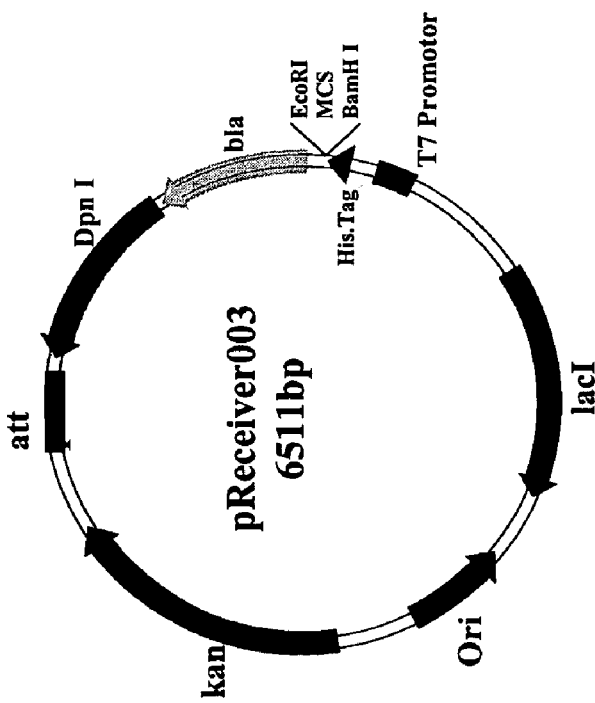
Fig. 22

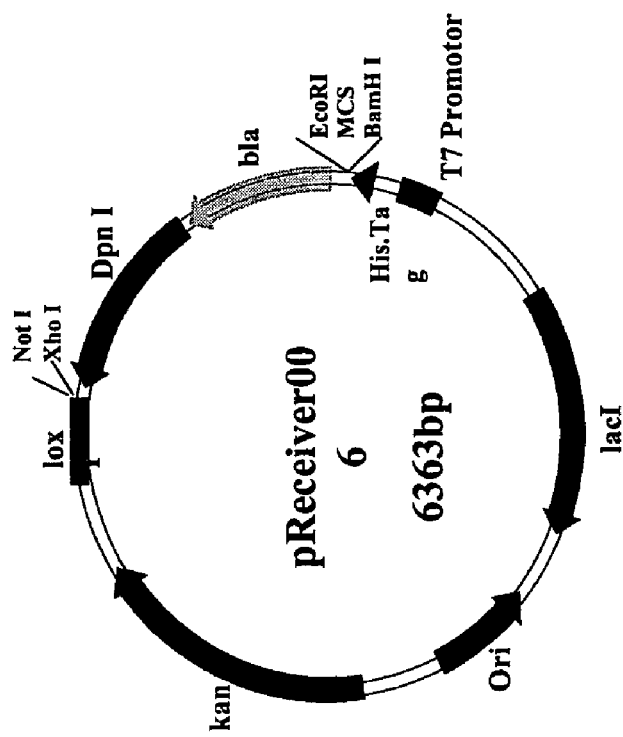
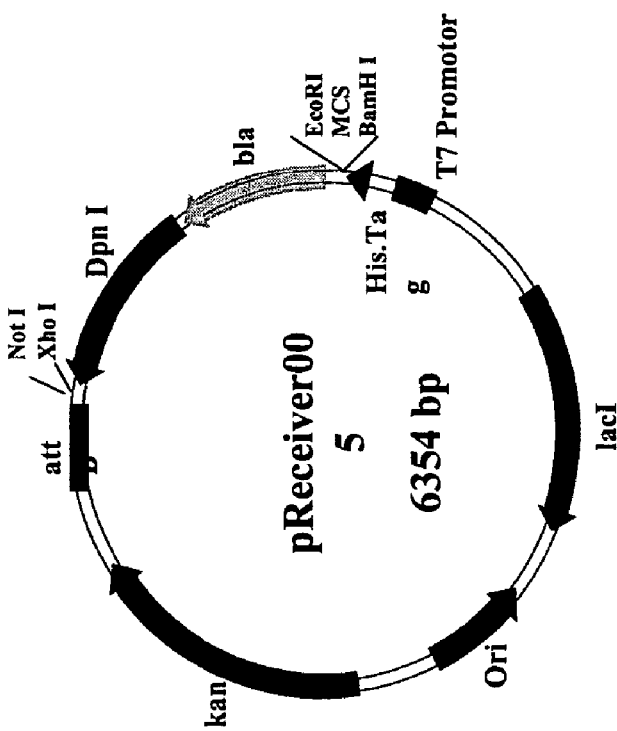
Fig.23

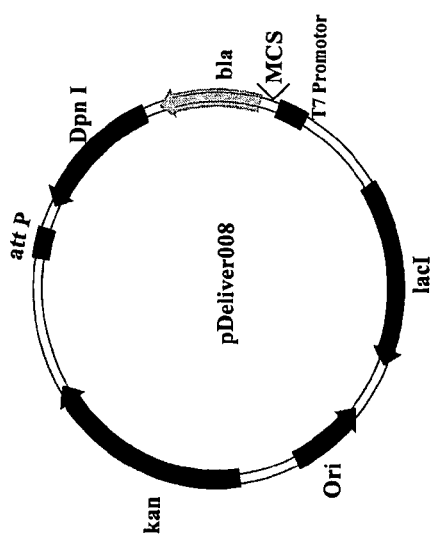

pDeliver008 MCS:

AGATCTCGATCCCGCGAAATTAATACGACTCACTATAGGGAATTGTGAGCGGATAACAATTCCCCTCTAGAAGGAGTTCGAACCC

T7 promotor                                             lac operator                     XbaI  rbs   NspV
                                                                                                                                                                                                                                 XmnI pDeliver008x MCS:

AGATCTCGATCCCGCGAAATTAATACGACTCACTATAGGGAATTGTGAGCGGATAACAATTCCCCTCTAGAAGGAGTTCGGTACCC

T7 promotor                                             lac operator                     XbaI  rbs   KpnI
                                                                                       XmnI EcoRI pDeliver008y MCS:

AGATCTCGATCCCGCGAAATTAATACGACTCACTATAGGGAATTGTGAGCGGATAACAATTCCCCTCTAGAAGGAGTTTAAACACC

T7 promotor                                             lac operator                     XbaI  rbs   PmeI

Fig. 25

MCS:

pReceiver100

--//GGTTTAGTGAACCGTCAGATCCGCTAGCCCGGGGCCACCCCTATTTGTTTATTTTCTAAATACATTCAAATATGTATCCGC//--

<u>NheI SmaI</u>      bla →
         <u>NarI</u> pReceiver100x

-//GGTTTAGTGAACCGTCAGATCCGCTAGCCCGGGCAA<u>TGTACA</u>CCTATTTGTTTATTTTCTAAATACATTCAAATATGTATCCGC//-

<u>NheI SmaI</u>    <u>BsrGI</u>    bla →
                <u>MfeI</u>

METHODS AND NUCLEIC ACID VECTORS FOR RAPID EXPRESSION AND SCREENING OF CDNA CLONES

FIELD OF THE INVENTION

This invention relates to recombinant DNA technology. More specifically, this invention provides recombinant DNA vectors and methods for cloning and expressing nucleic acid molecules by using a combination of site-specific recombination and joining reactions such as endonuclease restriction digestion and ligation. The DNAs, vectors and methods can be used for inserting, exchanging, and transferring a variety of DNA segments both in vitro and in vivo.

The present invention discloses a cloning strategy that takes advantage of both site-specific recombination, and technologies for digesting and joining nucleic acid molecules such as restriction enzyme digestion and ligation, for the transfer of a DNA of interest from one molecule or vector (gene donor) to another molecule or vector (gene receiver), to produce a nucleic acid molecule that contains the desired elements from both the donor and receiver molecules, such as an expression vector that is able to express the gene of interest.

BACKGROUND OF THE INVENTION

Recent advances in genomics technology have created an enormous wealth of information about living organisms at the DNA or gene level. Challenges currently facing the biotechnology community are to elucidate the function of these DNAs or putative genes, which often requires the study of these genes at the protein level. As functional genomics research usually involves the generation and subsequent sequencing of cDNA clones, further functional and/or structural study of these clones at the protein or amino acid level often involves expressing these genes or DNA inserts in a suitable system in a sufficient amount and suitable form. These cDNA clones, however, are often not suitable for protein expression purposes, and the cDNA inserts in these clones need to be subcloned into a suitable expression vector. Because the sheer number of clones in need to be studied, traditional cloning and subcloning methods clearly are not adequate because of the need for individual subcloning strategies and their low efficiency. There is currently an increasingly pressing need for technologies that allow rapid, precise, and directional gene transfer from one vector (often termed a "donor vector"), such as the cDNA clones from a genomics research project, into a suitably adapted expression vector (the "acceptor vector"). Preferably, the methodology and acceptor vector should allow (1) the elimination of individual, often awkward and time-consuming subcloning strategies, (2) rapid screening of hundreds of genes at a time (3) in a variety of host organisms or cell lines. Furthermore, the new methods and vectors should be suitable for studies at genome-wide scale using informatics and automation.

Strategies and commercial products already exist in the prior art that utilizes site-specific recombination systems, or restriction endonuclease digestion and subsequent ligation. Restriction endonuclease digestion and ligation have been used in molecular biology and biotechnology for a very long time and are well-established technology. Likewise, the recombination process and related proteins are also well known to those skilled in the art and numerous recombination systems from various organisms have been described, see, e.g. Landy, A., 1993, Current Opinion in Biotechnology 3:699–707; Abremski et al., 1986, J. Biol. Chem. 261:391; Hoess et al., 1986, Nucleic Acids Research 14:2287; Campbell, 1992, J. Bacteriol. 174:7495; Qian et al., 1992, J. Biol. Chem. 267:7794; Araki et al., 1992, Biol. 225:25; Maeser et al., 1991, Mol. Gen. Genet. 230:170–176.

The use of phage lambda enzymatic site-specific recombination and wild-type recombination sites attB and attP for the construction of a DNA segment to produce a protein in *E. coli* was disclosed in U.S. Pat. No. 4,673,640. Intramolecular recombination between wild type attP and attB sites which flank a promoter with lambda recombination system in vivo was described by Hasan et al. (1987, Gene 56:145–151).

Palazzolo et al., 1990, Gene 88:25–36 discloses phage lambda vectors having bacteriophage lambda arms positioned outside a cloned DNA sequence and between wild-type loxP sites. *E. coli* cells that express the Cre recombinase is transformed by these phage vectors, resulting in recombination between the loxP sites and in vivo excision of the plasmid replicon, including the cloned cDNA.

A method for inserting partial genomic DNA into expression vectors having a selectable marker was described in Posfai et al. (1994, Nucl. Acids Res. 22:2392–2398). The marker was flanked by two wild-type frt recognition sequences and FLP recombinase in the cells integrates the vectors into the genome at predetermined sites.

U.S. Pat. No. 5,434,066 discloses the use of site-specific recombinases such as Cre for DNA containing two loxP sites for in vivo recombination between the sites.

Waterhouse et al. (Nucleic Acids Res. 21 (9):2265 (1993)) discloses an in vivo method to clone light and heavy chains of a particular antibody in different phage vectors, using recombination between loxP and loxP 511 sites. The Cre protein acts in the host cells on the two parental molecules (one plasmid, one phage) and produce four products in equilibrium: two different cointegrates (produced by recombination at either loxP or loxP 511 sites), and two daughter molecules, one of which was the desired product.

Schlake et al. (Biochemistry 33:12746–12751 (1994)) discloses an in vivo method for exchanging expression cassettes at defined chromosomal locations, each flanked by a wild type and a spacer-mutated FRT recombination site. A double-reciprocal crossover was mediated in cultured mammalian cells by using this FLP/FRT system for site-specific recombination.

The transposase family of enzymes have also been used to transfer genetic information between replicons. Transposons are structurally variable, being described as simple or compound, but typically encode a recombinase gene flanked by DNA sequences organized in inverted orientations. Integration of transposons can be random or highly specific. Representatives such as Tn7, which are highly site-specific, have been applied to the in vivo movement of DNA segments between replicons (Lucklow et al., J. Virol. 67:4566–4579 (1993)).

Devine et al. (Nucl. Acids Res. 22:3765–3772 (1994) disclose a system that makes use of the integrase of yeast TY1 virus-like particles. The DNA segment of interest is cloned, using standard methods, between the ends of the transposon-like element TY1. In the presence of the TY1 integrase, the resulting element integrates randomly into a second target DNA molecule.

U.S. Pat. No. 6,410,317 B1, to Farmer et al. discloses a method for producing expression vectors using the Cre recombinase. In this system, the gene of interest is inserted into a polylinker site, or multiple cloning site ("MCS"), via restriction endonuclease digestion and ligation, of a "donor vector." The MCS is flanked by two loxP sites, the specific recognition site of Cre Recombinase of bacteriophage P1, oriented in the same direction. In the presence of Cre recombinase, the gene of interest of the donor vector is transferred to an "acceptor" or a receiver vector which contains one loxP site at which the gene of interest will be inserted. The acceptor vector also contains various other elements generally required of an expression vector, such as a suitable promoter, a suitable marker gene or genes, an appropriate peptide tag, and replication origin. The acceptor vector is thus converted into a desired expression vector, which is disclosed to be suitable for expression in many expression systems.

U.S. Pat. No. 6,277,608 B1, to Hartley et al., discloses an alternative strategy using a system of at least a recombinase, an insert donor and a vector donor. The insert donor contains two site-specific recombinase recognition sites, each of which is recognized by its own recombinase, but which do not recombine with each other. Similarly, the vector donor also contains two site-specific recombinase recognition sites, recognized by the same two recombinase. The recognition site for one recombinase on the insert donor is capable of recombining with the recognition site for the same recombinase on the vector donor, and likewise, the recognition site for the other recombinase is capable of recombining with the recognition site for that recombinase. In the presence of one recombinase, the two donor molecules recombine to form a circular cointegrate, which in the presence of the second recombinase resolves into two circular molecules, one the desired expression vector, and the other a by-product. The specific recombinase/recognition site system exemplified in Hartley et al. is the well-knonw Integrase/att system from bacteriophage λ (see e.g. Landy, 1993, *Current Opinions in Genetics and Devel.* 3:699–707).

International Patent Application WO 02/46372 (Chestnut et al., 2002) discloses a method for cloning two or more different nucleic acid molecules simultaneously using vectors having multiple recombination sites and/or multiple topoisomerase recognistion sites. Published U.S. patent application 20030124555 (Brasch et al.) discloses a method for cloning a population of nucleic acid molecules on interest, specifically a cDNA library into a vector which has one or two recombination sites. The method requires two or more recombination steps and multiple recombination sites. These cloning methods utilizing site-specific recombination, however, require an initial construction of a donor vector that contains the desired DNA segment(s) or insert(s), followed by the transfer of the segment(s) into a second, desired expression vector for the expression of the segment(s).

In addition, in some the above methods, the DNA of interest is transferred to the acceptor vector via site-specific recombination. Invariably, the promoter and other regulatory elements of the expression vector are placed on one side (upstream) of the newly formed recombination recognition site(s), while the insert sequence or DNA of interest is invariably on the other side (downstream) of the same recombination recognition site. As a consequence, the nucleotides of the recombination recognition site(s) are placed in-between the promoter (and/or other expression signals) and the coding sequence of the DNA of interest, and may be expressed as well, resulting in additional and unwanted amino acid residues in the expressed product. For example, in the Integrase/att cloning system, the protein expressed from the insert DNA contains an extra fragment of at least eight (8) amino acids as a result of the expression of the DNA sequences of the attsite, that is flanked by a DNA sequence encoding a tag peptide and the insert DNA. In some cases, these extra amino acids are undesirable because they may affect efficiency of the protein expression, and the structure and function of the expressed protein. They may also affect the correct folding and/or configuration of the protein, and affect or change the biochemical and biophysical properties of the fusion protein, which is of great concern to investigators.

Another undesirable aspect of the prior art recombination cloning method relates to the need to synthesize long oligonucleotide primers for the cloning process. Invariably, the gene of interest needs to be amplified using the polymerase chain reaction (PCR) and then cloned into a vector. The PCR primers are engineered to contain, in addition to the gene-specific sequence at the 3' end, linker sequences at the 5' end containing the recombinase recognition site. These linker sequences are suitable to allow for subsequent site-specific recombination reactions. Because these linker sequences often are dozens of nucleotides long, their synthesis adds considerable costs to the cloning efforts. Furthermore, the longer the primers, the higher the possibility of errors in the primers introduced during the chemical synthesis.

In some of the recombination cloning methods described above, an in vivo step is required for the recombination reaction in order to exchange the insert DNA from one vector to another. An in vivo recombination is a very complex process that involves homologous recombination, Because of the DNA recombination repair machinery of the cell, there is a high risk that the genetic information carried by the insert DNA may be changed by these recombination cloning.

Furthermore, all of the above recombination cloning and subcloning approaches require at least two separate cloning processes in order to position expression signals and a DNA of interest in an expression vector.

There is therefore a need for alternative and improved methods and vectors for cloning and shuttle cloning or subcloning.

SUMMARY OF THE INVENTION

An object of the present invention is to provide improved cloning methods over classical cloning methods. The present invention provides simple cloning methods that avoid the numerous steps required of classical cloning methods and prior methods using site-specific recombination. As will become clear in the detailed description below, the inventive methods enable the nucleic acid fragment to be cloned in the desired orientation regardless whether the joinable ends are blund ends or sticky ends. Furthermore, the use of irreversible joinable ends also makes it possible to conduct the many reactions (recombination, digestion and ligation) in one reaction vessel.

For the construction of an expression vector, especially for use in prokaryotes such as *E. coli*, prior art recombination cloning methods require at least two recombination cloning vectors and two or more recombination steps. Because of the requirement of a ribosome binding site (e.g. Shine-Dalgano sequence for prokaryotes and the Kozak Sequence for eukaryotes), prior art recombination methods are unsatisfactory. This is because in the vector the promoter and ribosome binding site (RBS) are located upstream of the recombination site, and after recombination that inserts a gene into the vector, the newly formed recombination site renders the distance between the RBS and start codon ATG of coding sequence too far for efficient translation. This is so even if the recombiantion sites are short in size (such as attB and loxP).

The present invention provides suitable linker sequences (e.g. SEQ ID NO: 3) that comprise an RBS and required spacer sequence between the RBS and the start codon of the coding sequence. These linker sequences are incorporated into the nucleic acid fragment of interest and/or a suitable vector. When a vector contains the adapter downstream of a suitable promoter (e.g T7 for E. coli host), a joining reaction of the invention (as described below) will place the fragment of interest in a position such that the start codon ATG is be in suitable distance from the RBS, resulting in an expression vector that can be directly used for transformation and expresses the fragment of interest with high efficiency.

The present invention overcomes the above prior art shortcomings by providing a novel cloning method using a combination of site-specific recombination and nucleic acid molecule joining reactions, especially ligation. According to the present invention, a nucleic acid molecule or fragment of interest is transferred from Parent Molecule 1 to Parent Molecule 2,wherein Parent Molecule 1 comprises the nucleic acid molecule or fragment of interest and Parent Molecule 2 comprises at least one functional element that is able to influence the transcription, translation or replication of the nucleic acid molecule or fragment of interest, or for transferring a nucleic acid molecule or fragment of interest from Parent Molecule 2 to Parent Molecule 1 wherein Parent Molecule 2 comprises the nucleic molecule or fragment of interest and Parent Molecule 1 comprises at least one functional element that is able to influence the transcription, translation or replication of the nucleic acid molecule or fragment of interest, wherein Parent Molecule 1 may be linear or circular, and Parent Molecule 2 may be linear or circular; wherein Parent Molecule 1 comprises a first recombination site and Parent Molecule 2 comprises a second recombination site; wherein Parent Molecule 1 if linear comprises a first joinable end, and if circular comprises a first region that can be converted into a first joinable end; and wherein Parent Molecule 2 if linear comprises a second joinable end and if circular comprises a region that can be converted into a second joinable end; the method comprising mixing Parent Molecule 1 and Parent Molecule 2 in vitro; forming by either (a) site-specific recombination between the first and second recombination sites, or by (b)(i) joining the first and second joinable ends, or (ii) first converting the region or regions that can be converted into a joinable end or joinable ends, and then joining the joinable ends, an intermediate molecule comprising the nucleic acid molecule or fragment of interest and the at least one functional element; and processing the intermediate respectively by either (a) joining the first and the second joinable ends, or (b) by site-specific recombination between the first and second recombination sites, to form a circular Product Vector comprising the nucleic acid molecule or fragment of interest and the at least one functional element. The recombination step may occur first, followed by the restriction enzyme cleavage and ligation step or the joining step. Conversely, the joining step may occur prior to the recombination step. The combination of the recombination and joining steps makes the transferring the nucleic acid molecule or fragment of interest direct, and simplifies the cloning process.

Also disclosed are specific linkers, PCR primers comprising these linkers, and PCR methods, including nested PCR methods using these linkers. Specifically, the primers contain specific restriction endonuclease sites suitable for multiple cloning purposes, as well prokaryotic and eukaryotic translation signals. PCR amplification products by using the inventive methods summarized above and primers may be transferred into an expression vector in one step due to the close proximity of the translational signals and the coding region of the gene of interest (the PCR products).

CDS=coding sequence, or the gene of interest, NS=negative selection marker, MS=selection marker, JS=joined site.

Figure 5:
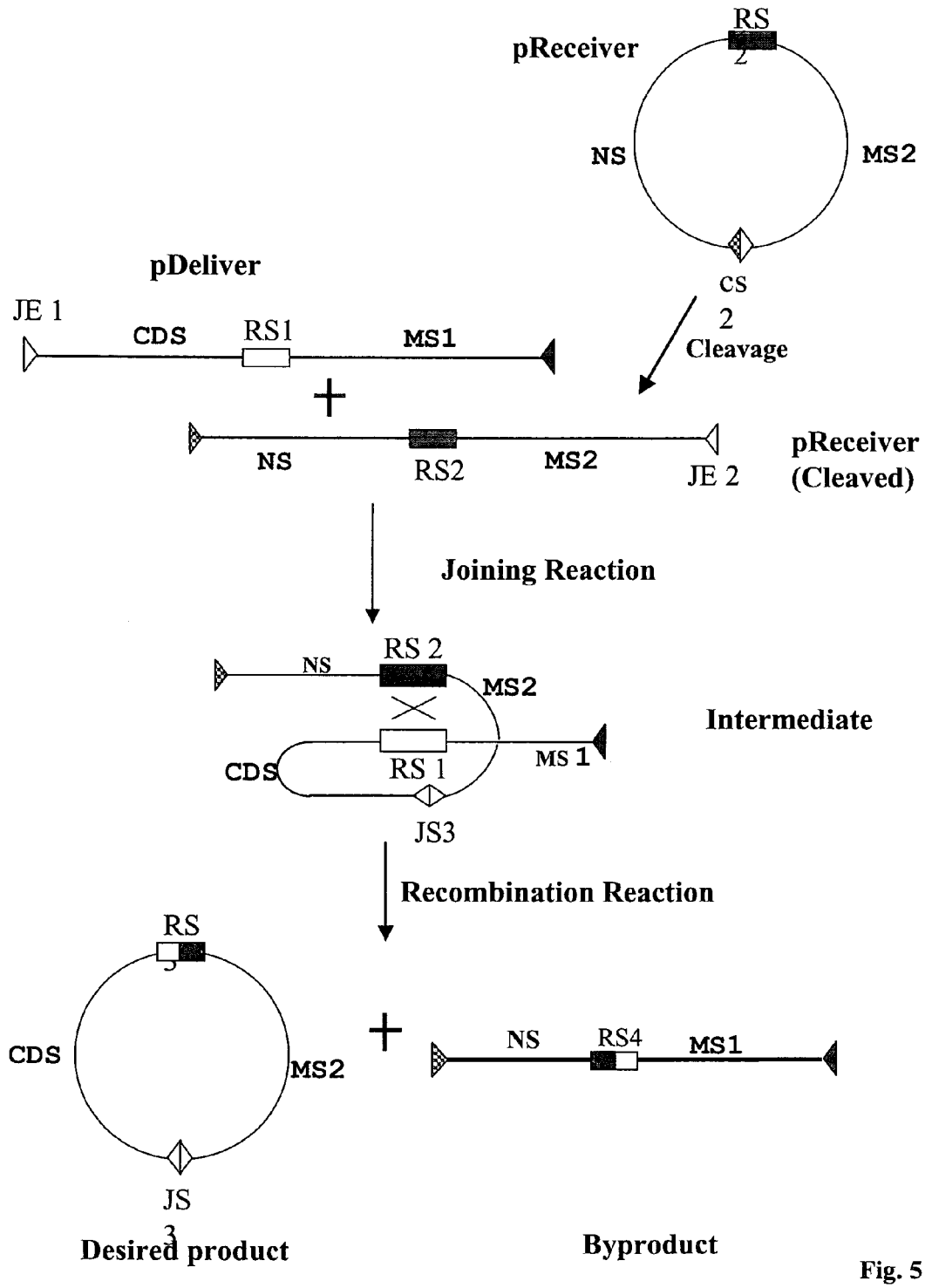
FIG. 5 shows more details of one embodiment shown in FIG. 1c. One circular Parent Molecule (pReceiver) is cleaved by restriction enzyme(s) at the cleavage site, producing a linear Parent Molecule with two joinable ends.
Figure 6:
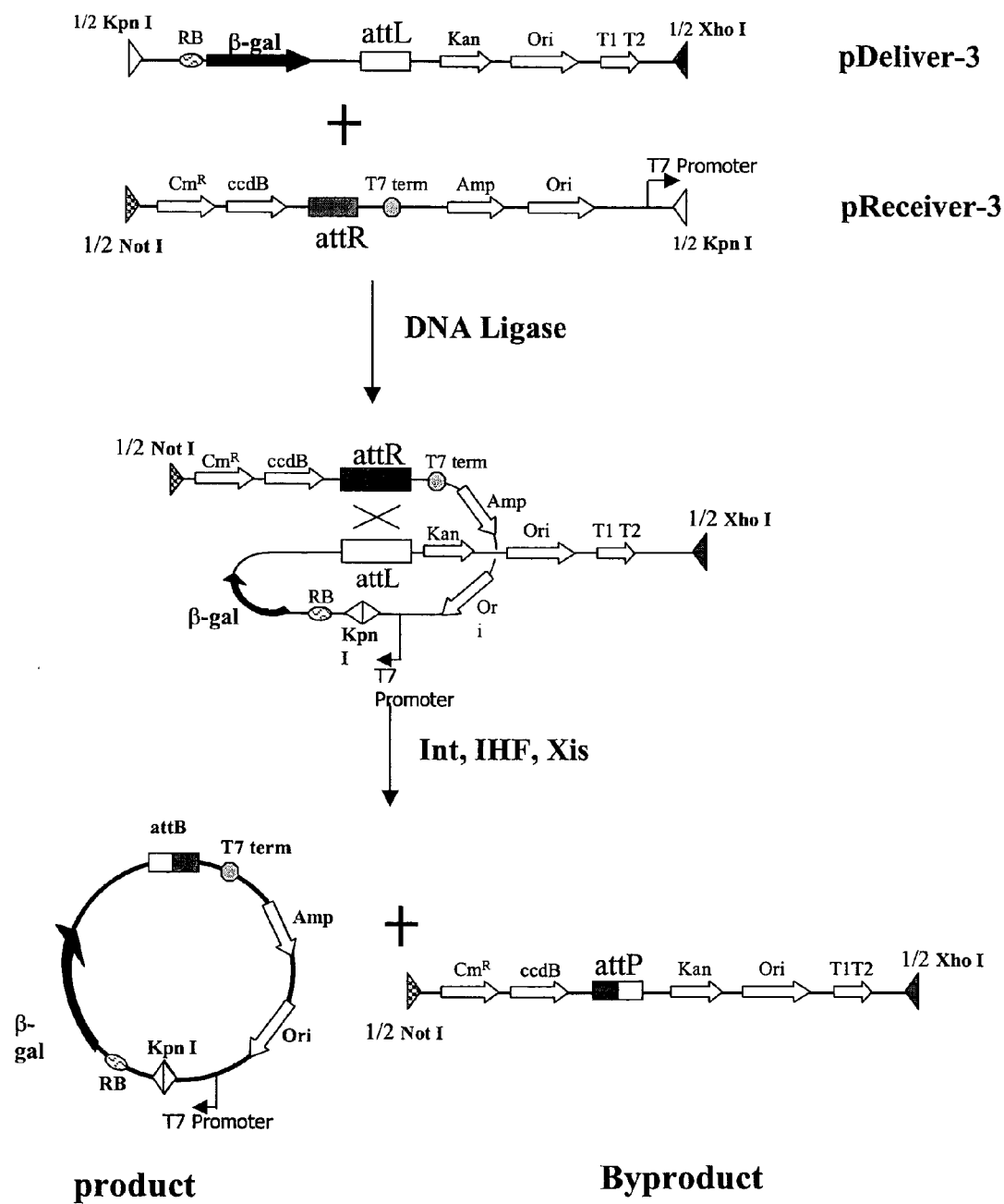
Figure 7:
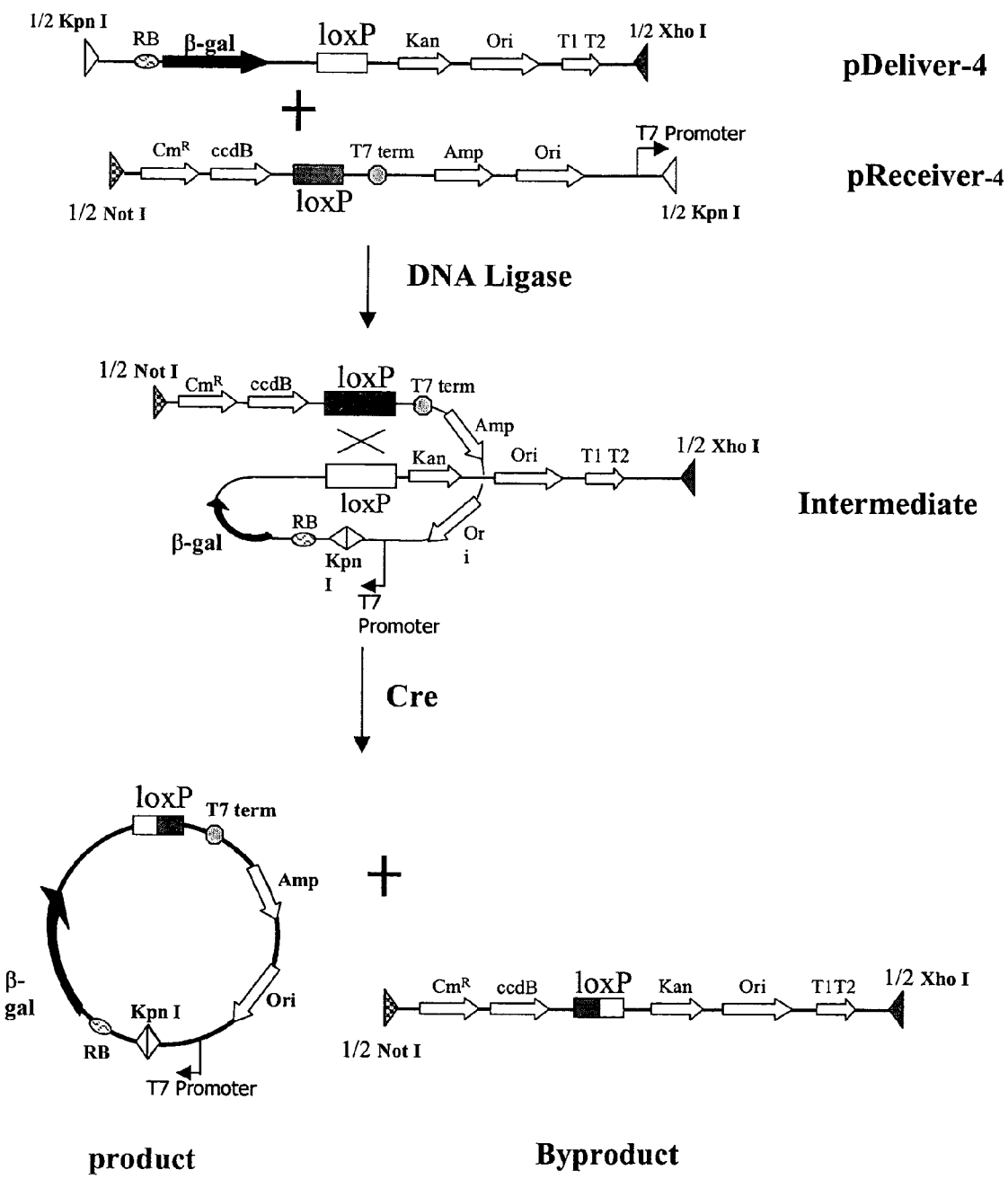

FIG. 6 is a more specific example of FIG. 5, Ligation of two ½ RE sites of Kpn I forms a linear Intermediate with a joined site (JS), and is followed by recombination between attR and attL site by recombinase proteins Int, IHF and Xis, resulting in a circular Desired Product FIG. 7 is a more specific example of FIG. 5, using loxP and Cre.

Figure 1A:
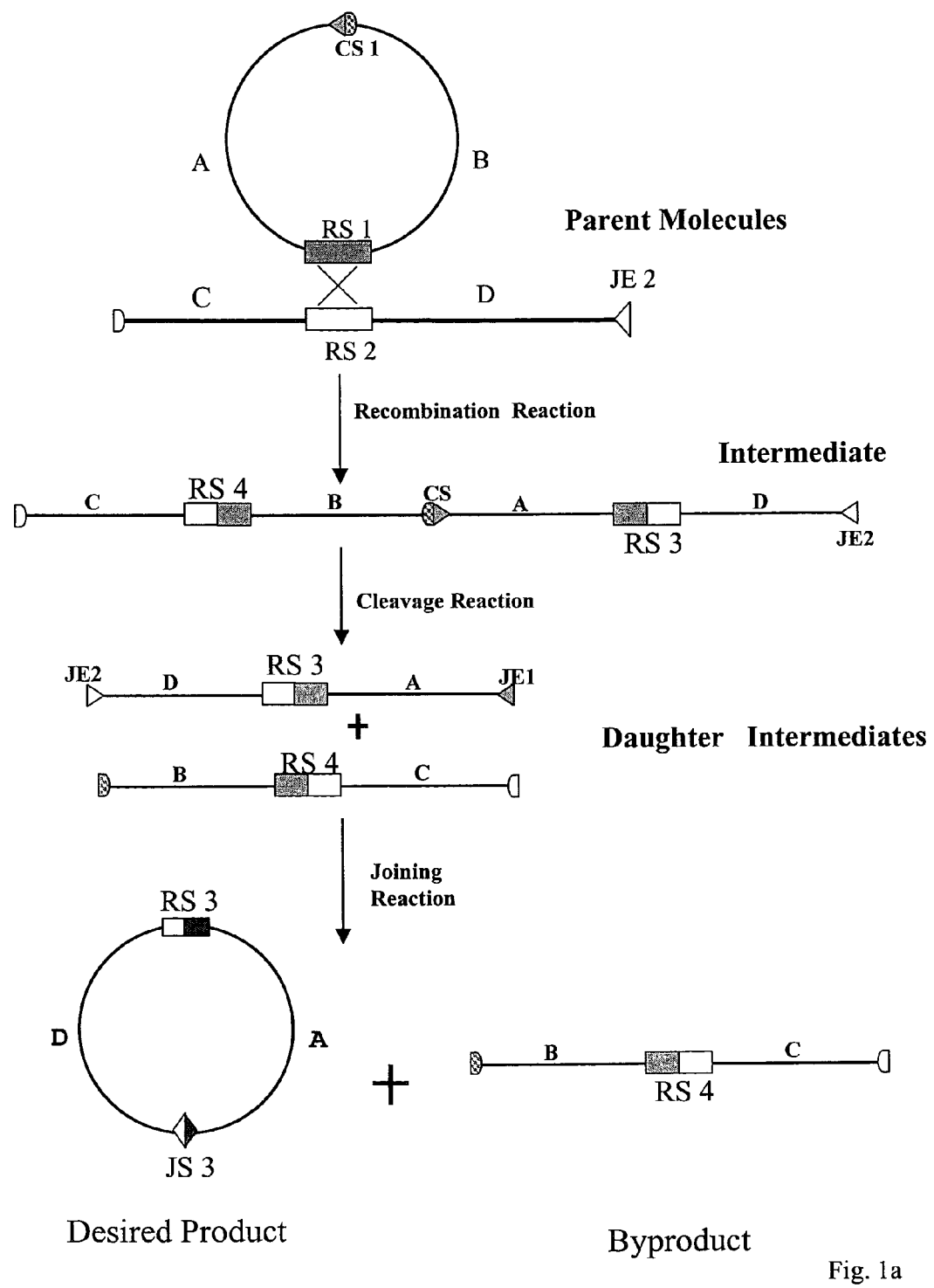
FIG. 1a depicts one embodiment of the present invention wherein one Parent Molecule is circular and contains a recombination site (RS1) and cleavage sites (CS1), and the other Parent Molecule is linear and contains a recombination site (RS2) and a joinable end (JE2). After recombination between the recombination sites (RS1 and RS2), a linear Intermediate is formed, which is then cleaved at CS1 by suitable restriction enzyme(s) to form two Daughter Intermediates. Only one of these two Daughter Intermediates comprises the desired segments A and D, as well as two Joinable Ends, JE1 and JE2. These two joinable ends are finally joined to form a circular Desired Product. It should be noted that if the cleavage at CS1 of Parent Molecule produces two joinable ends and the other Parent Molecule comprises two joinable ends, the linear Byproduct in this Figure may be circular.
Figure 8:
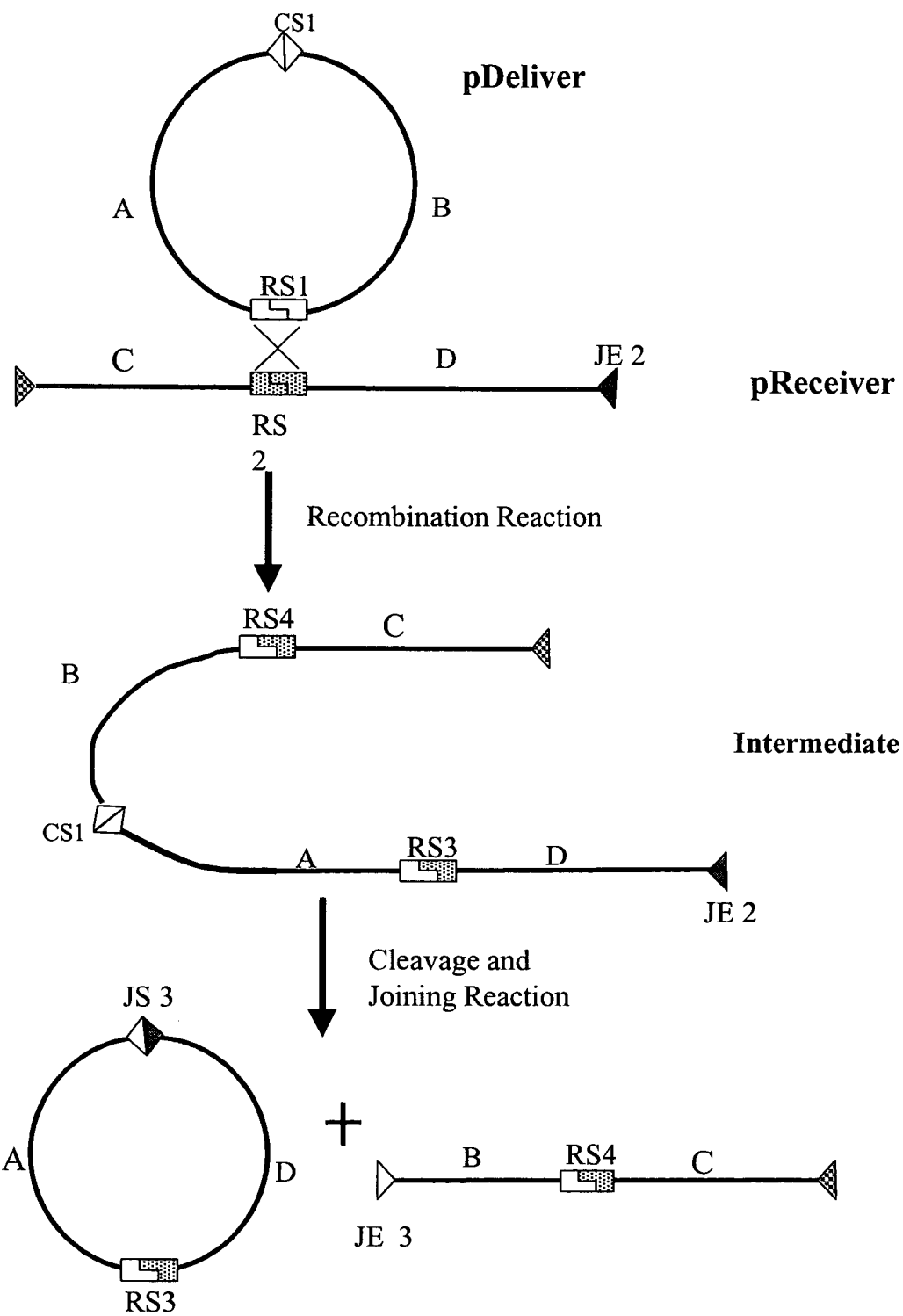

FIG. 8 is a specific example of FIG. 1a, wherein the cleavage and joining reaction occur in one step. Following the recombination reaction, cleavage at CS site by suitable restriction enzyme(s) generates a joinable end that is compatible with and joined to joinable end JE1, forming a circular Desired Products. JE3 generated from cleavage of CS and JE2 are not compatible.

Figure 9:
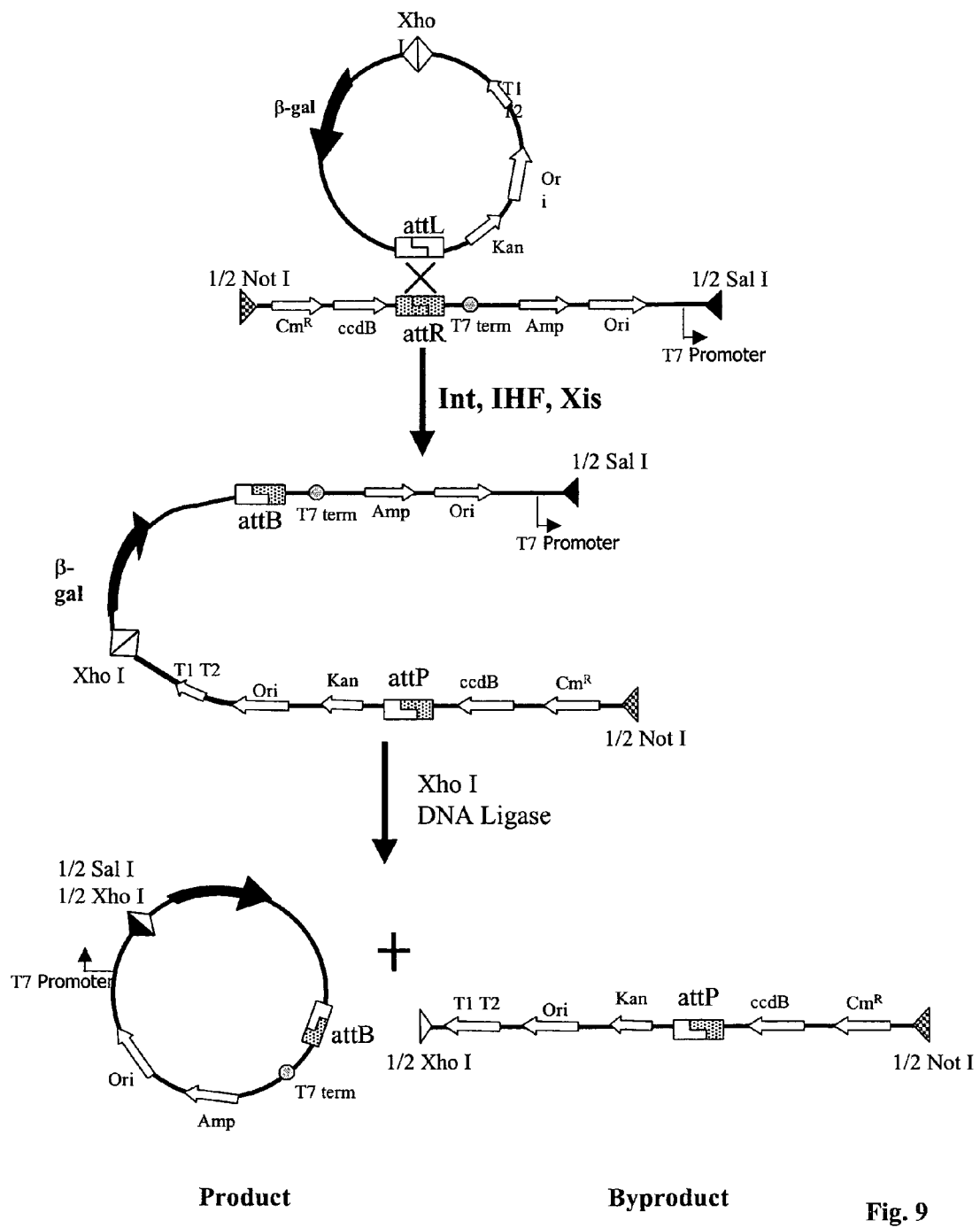

FIG. 9 is a more specific example of FIG. 8, using attR/attL and Int/IHF/Xis for recombination, and Xho I for cleavage and DNA ligase for joining reaction. The cleavage of the Xho site generates a joinable site (½XhoI) that is compatible with and joined to ½ Sal I site, forming a circular Desired Product. It shall be noted that the joining of ½ Xho I site to ½ Sal I site forms a new joined site (½ Xho and ½ Sal). Because the newly formed site can not be cleaved by Xho restriction enzyme, the cleavage and ligation reaction can be performed in one step.

Figure 10:
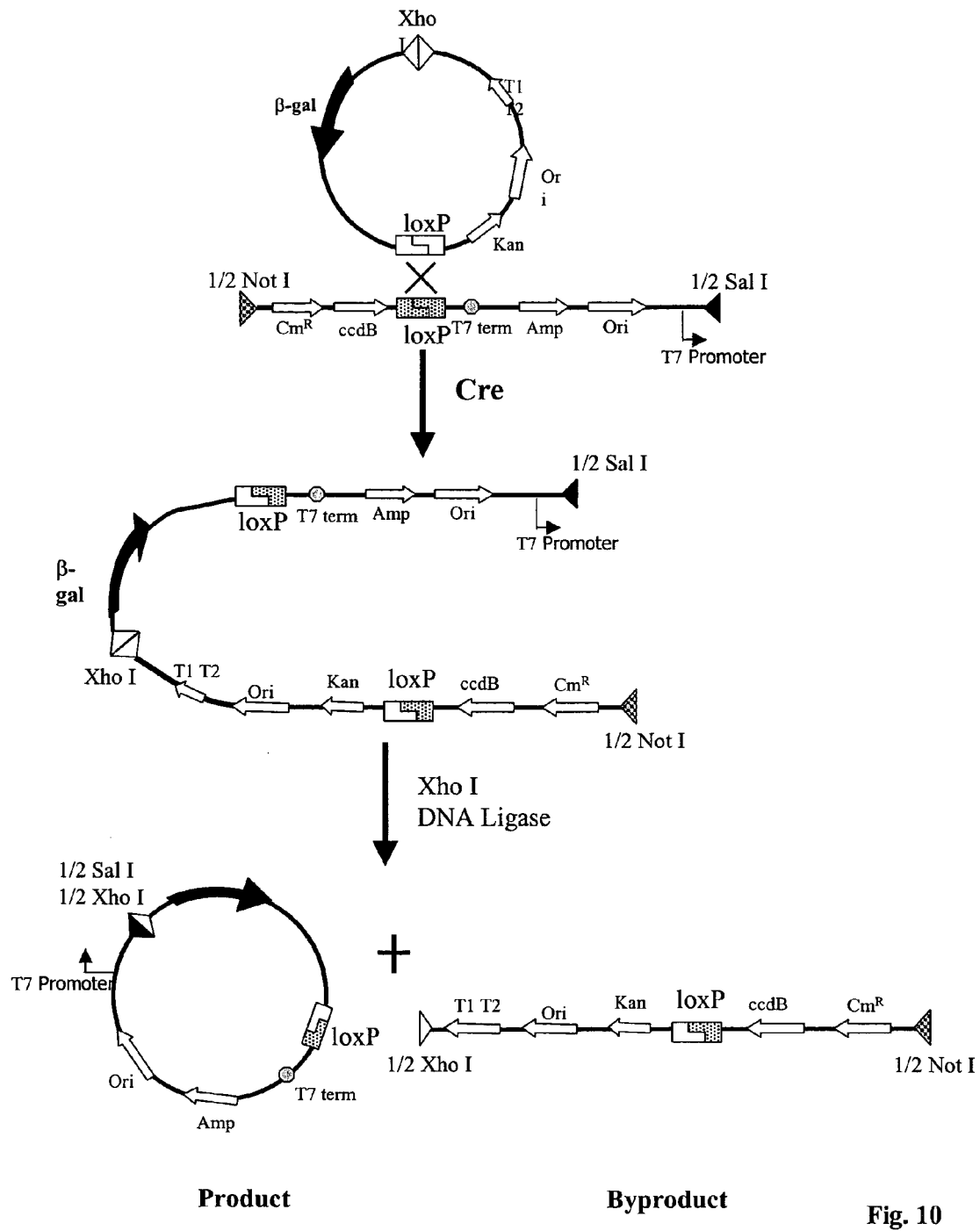

FIG. 10 is a more specific example of FIG. 8, using Lox/Cre for recombination and Xho I for cleavage and DNA ligase for joining. The cleavage of the Xho site generates a joinable site (½ XhoI) that is compatible with and joined to the ½ Sal I site, forming a circular Desired Product.

Figure 11:
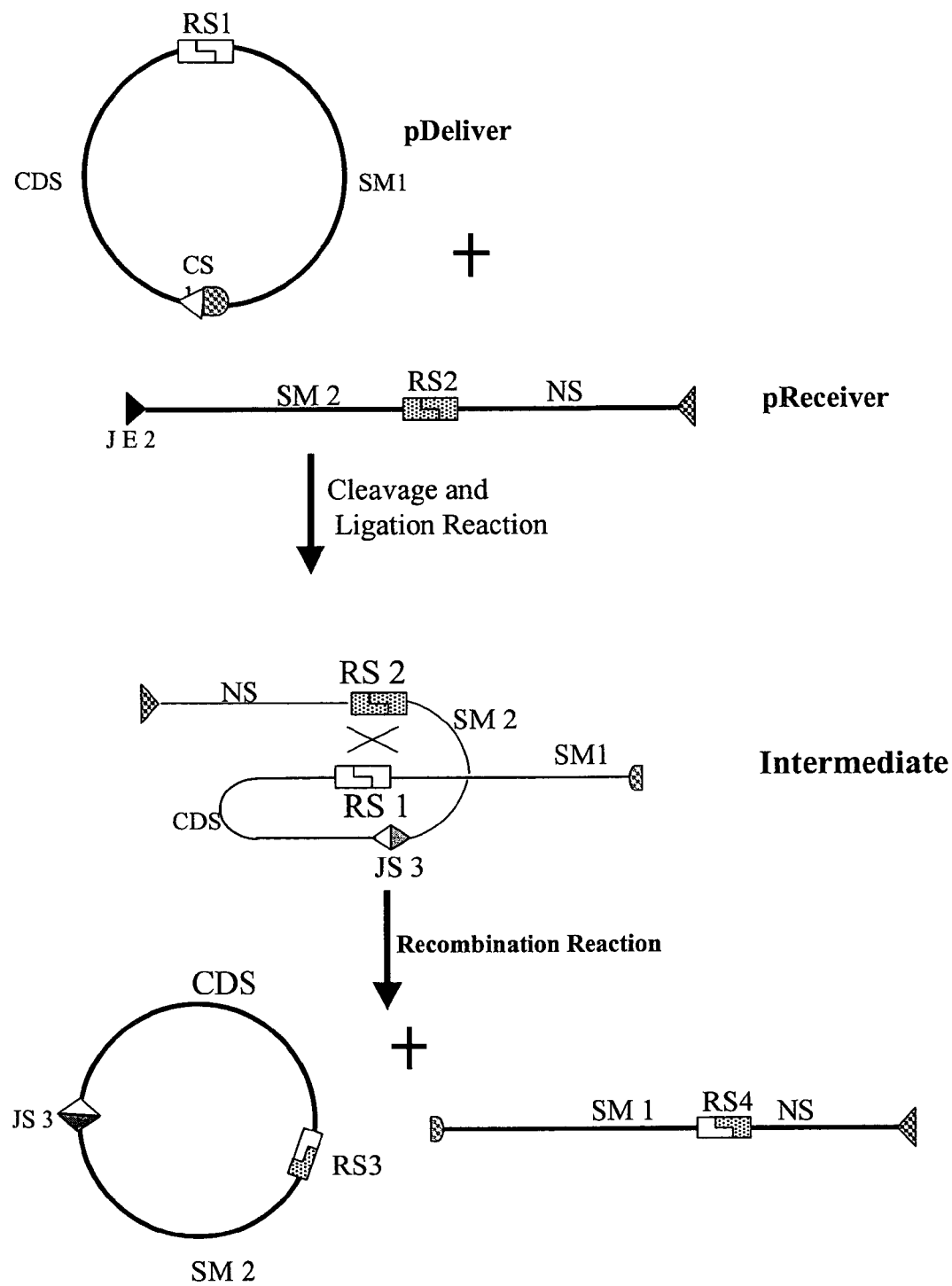

FIG. 11 depicts an embodiment of the invention where one of the Parent Molecules is circular, and the other is linear, and cleavage and joining reaction can occur together prior to the recombination step. CS1=cleavage site, JE1=joinable end 1; cleavage of CS1 site by suitable restriction enzyme(s) generates a joinable end that is compatible with and joined to JE1 site, forming joined site (JS) in the Daughter Intermediate that can not be cleaved by the same restriction enzyme(s) in the cleavage/joining reaction. The recombination reaction between two recombination sites, RS1 and RS2, of the Daughter Intermediate forms a circular Desired Product.

Figure 12:
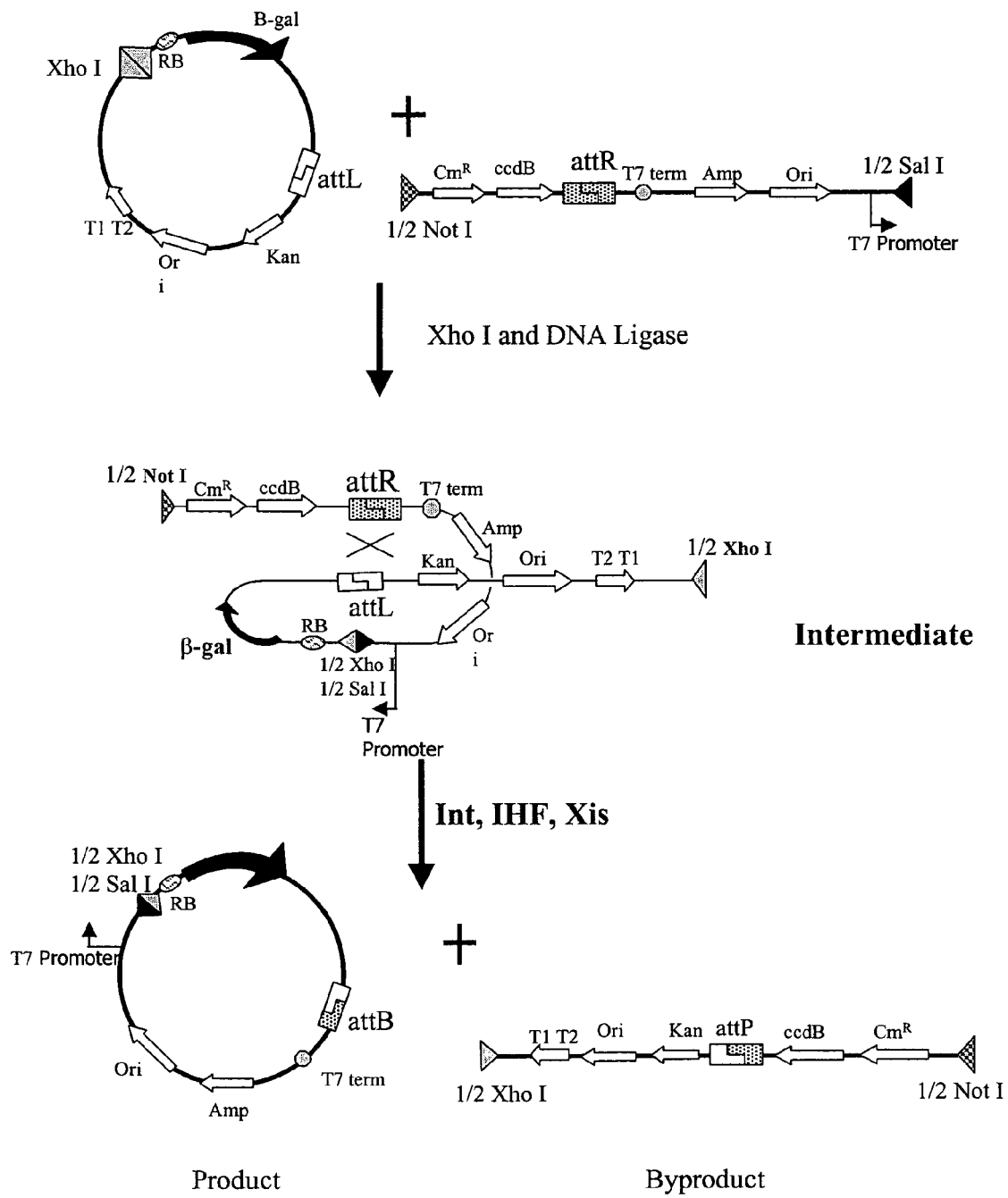

FIG. 12 is a more specific example of FIG. 11, using attR/attL and Int/IHF/Xis for recombination, and Xho I for cleavage and DNA ligase for the joining reactions.

Figure 13:
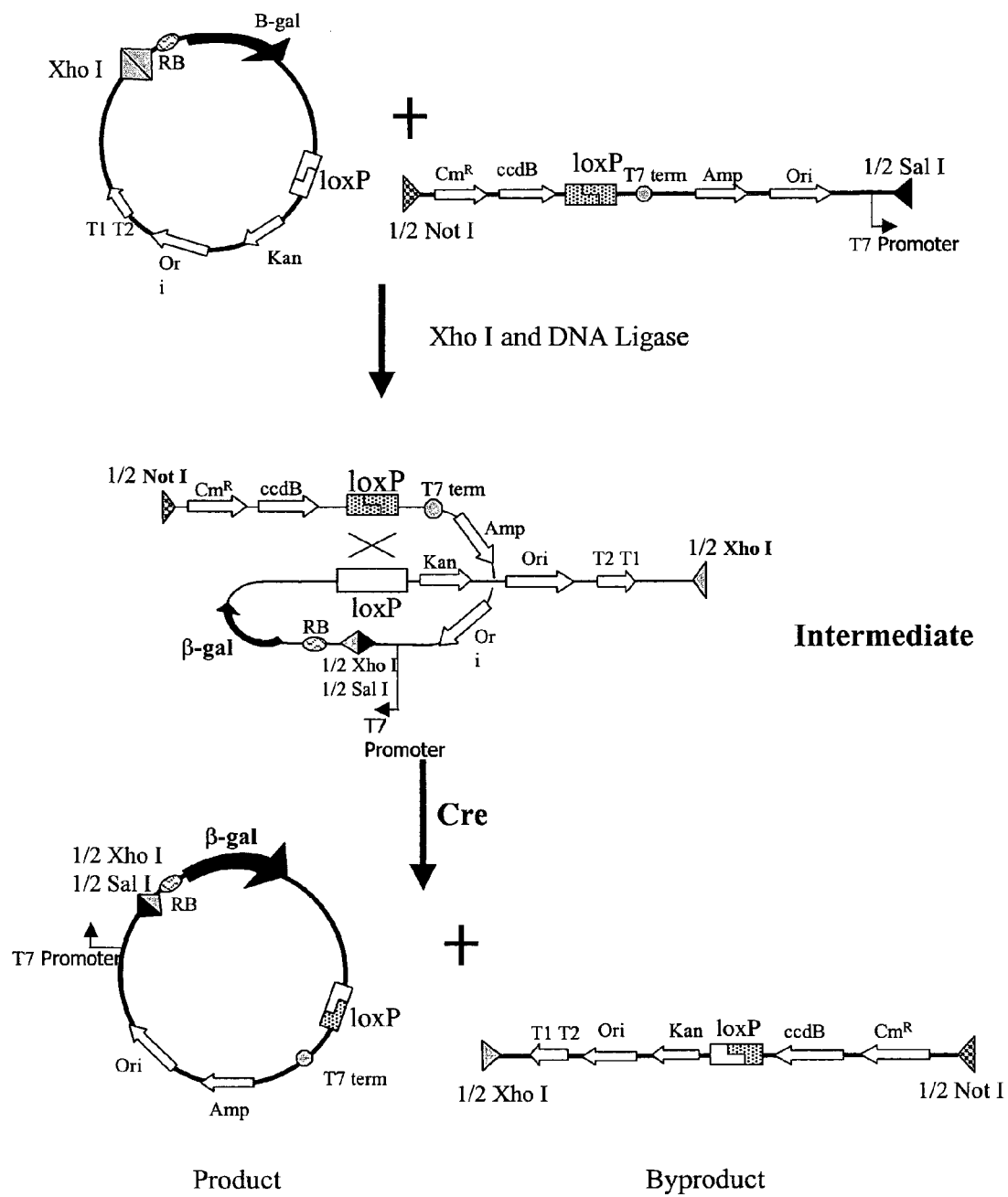

FIG. 13 is a more specific example of FIG. 11, using Lox/Cre for recombination and Xho I for cleavage and DNA ligase for joining the reaction.

Figure 1B:
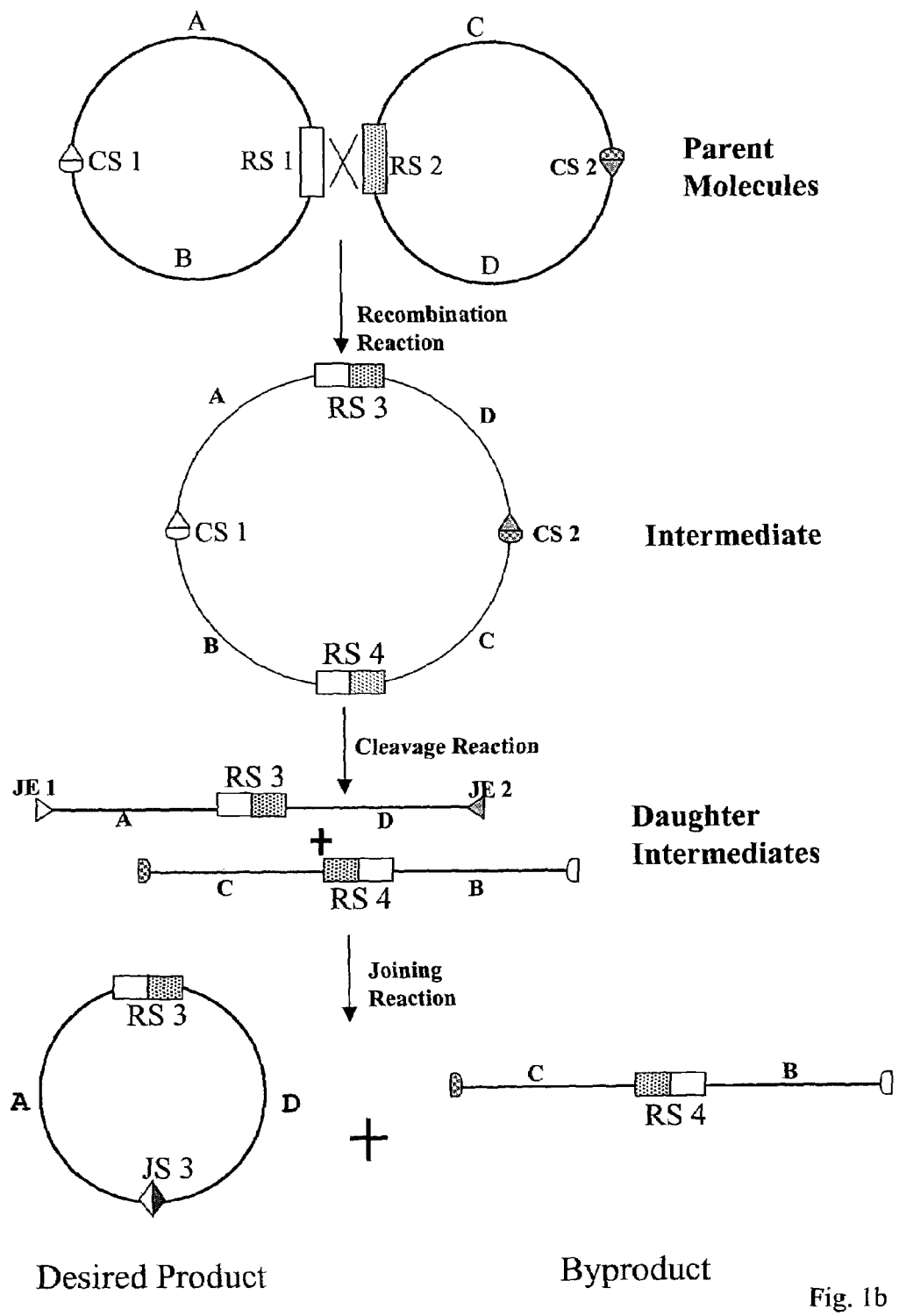
FIG. 1b depicts another embodiment of the present invention wherein both Parent Molecules are circular. After recombination between the recombination sites (RS1 and RS2), a circular Intermediate is formed, which is then cleaved at CS1 and CS2 by suitable restriction enzyme(s) to form two linear Daughter Intermediates. Only one of these two Daughter Intermediates comprises the desired segments A and D, as well as two Joinable Ends, JE1 and JE2. These two joinable ends are finally joined to form a circular Desired Product. It should be noted that iff the cleavage at CS1 and CS2 of the circular Intermediate produces two linear Daughter Intermediates, each linear Daughter Intermediate with two intra-molecule compatible joinable ends, the linear Byproduct in this Figure may be circular.
Figure 14:
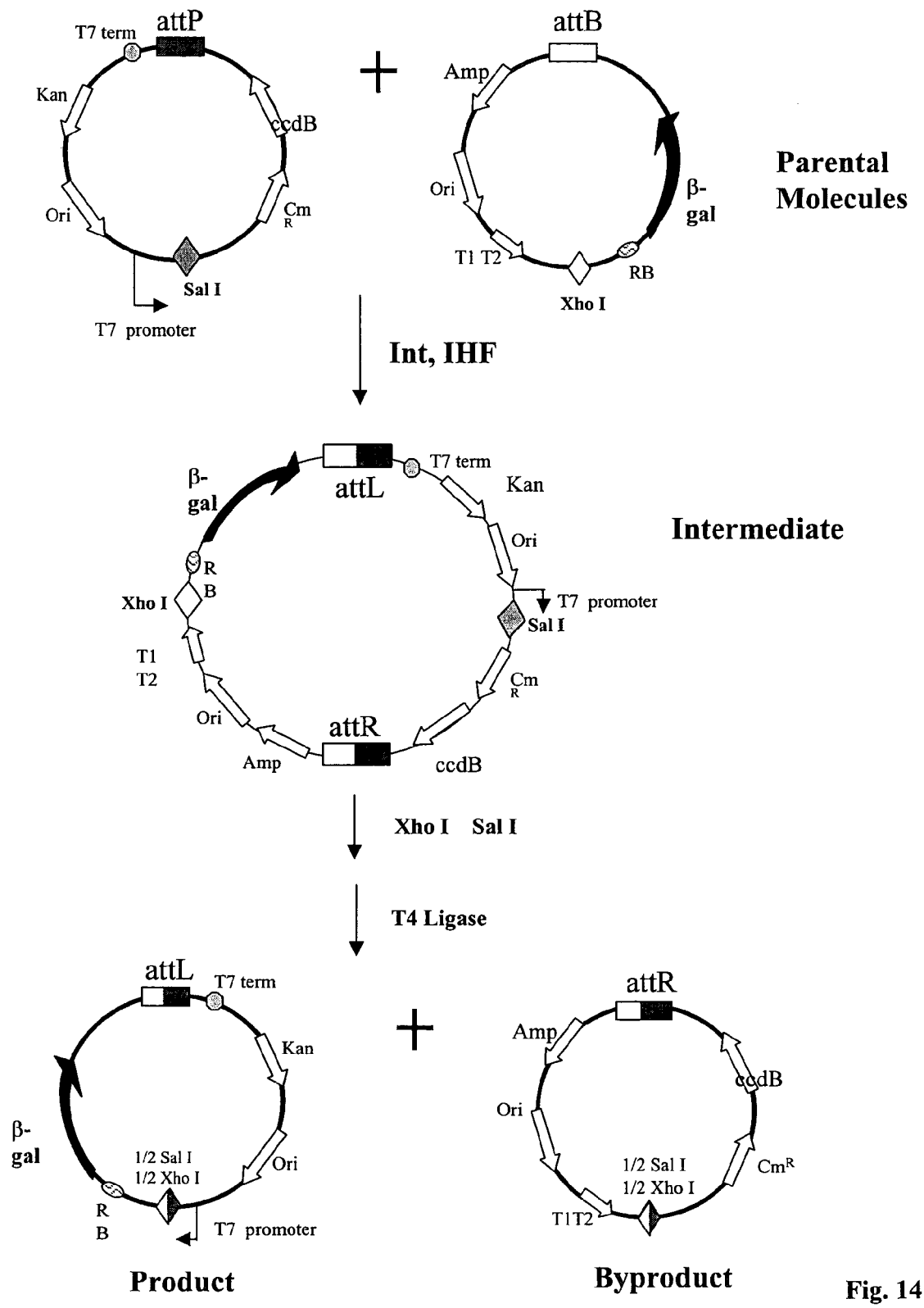

FIG. 14 is an example of the method shown in FIG. 1b, using attB/attP for recombination. Note that the cleavage and ligation reactions may occur in one step or in two steps.

Figure 15:
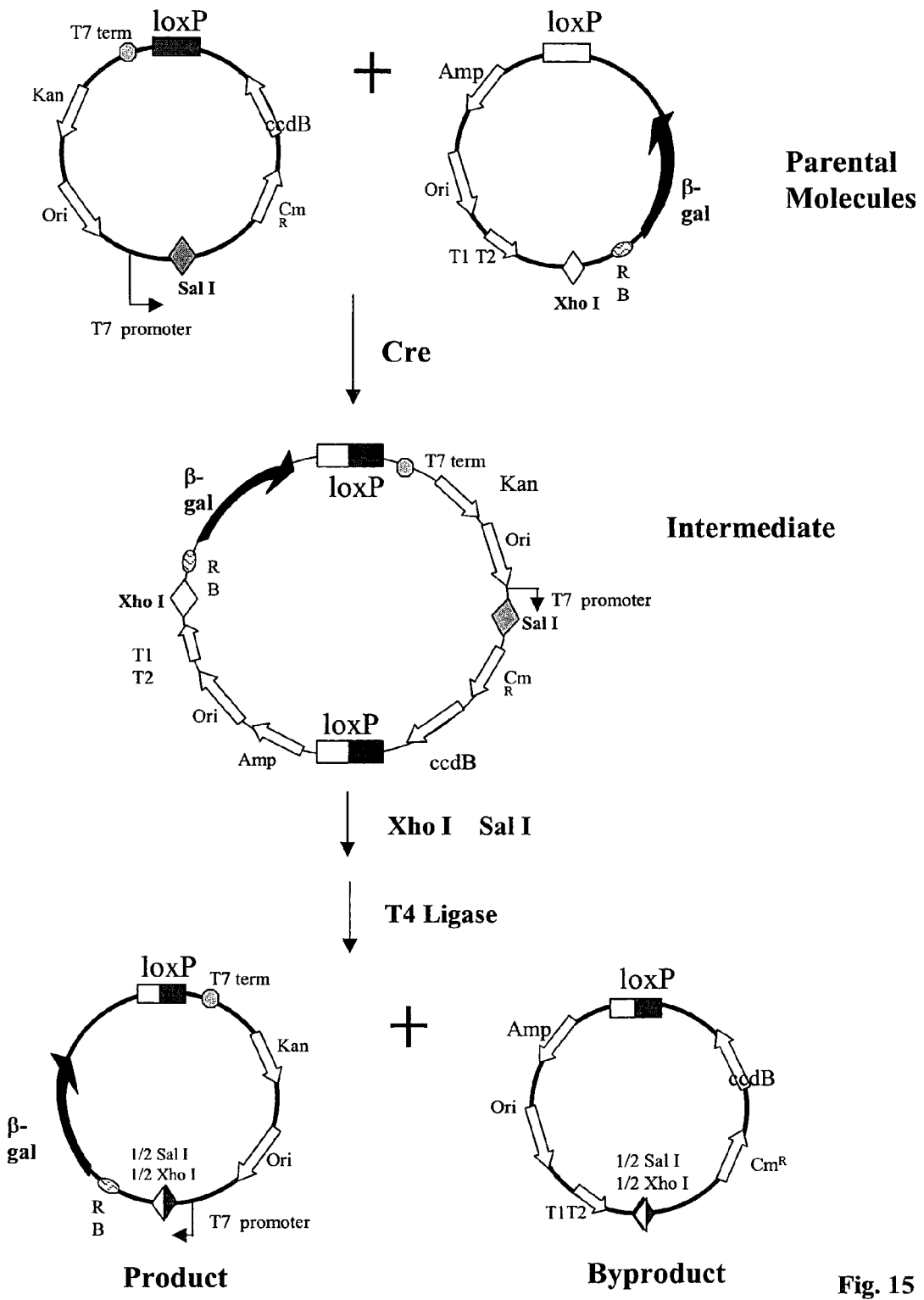

FIG. 15 is an example of the method shown in FIG. 1b, using loxP/Cre for recombination. Note that the cleavage and ligation reactions may occur in one step or in two steps. In FIGS. 14 and 15, the Desired Product can be selected by its carrying the selectable marker Kan.

Figure 16:
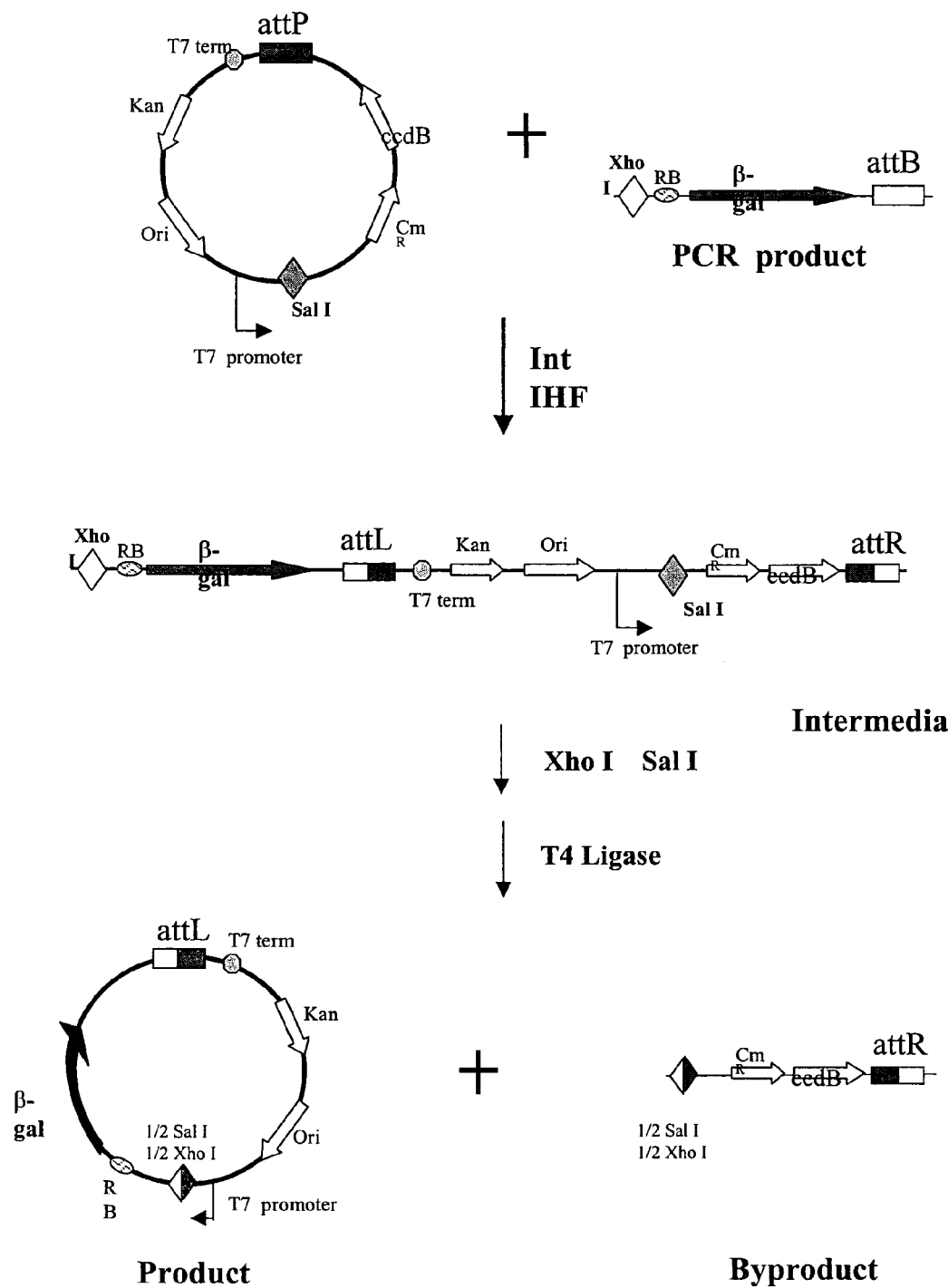

FIG. 16 is yet another example of the method shown in FIG. 1a, where an E. coli translation element, a ribosome binding site (RB) is located upstream of the coding sequence of the β-galactosidase gene (β-gal), flanked by a recognition site for restriction enzyme Xho I at one end and an attB site at the other. The recombination between attP and attB site by IHF and Int proteins followed by cleavage and ligation reaction forms a circular Desired Product, an expression vector for β-gal suitable for E. coli.

Figure 17:
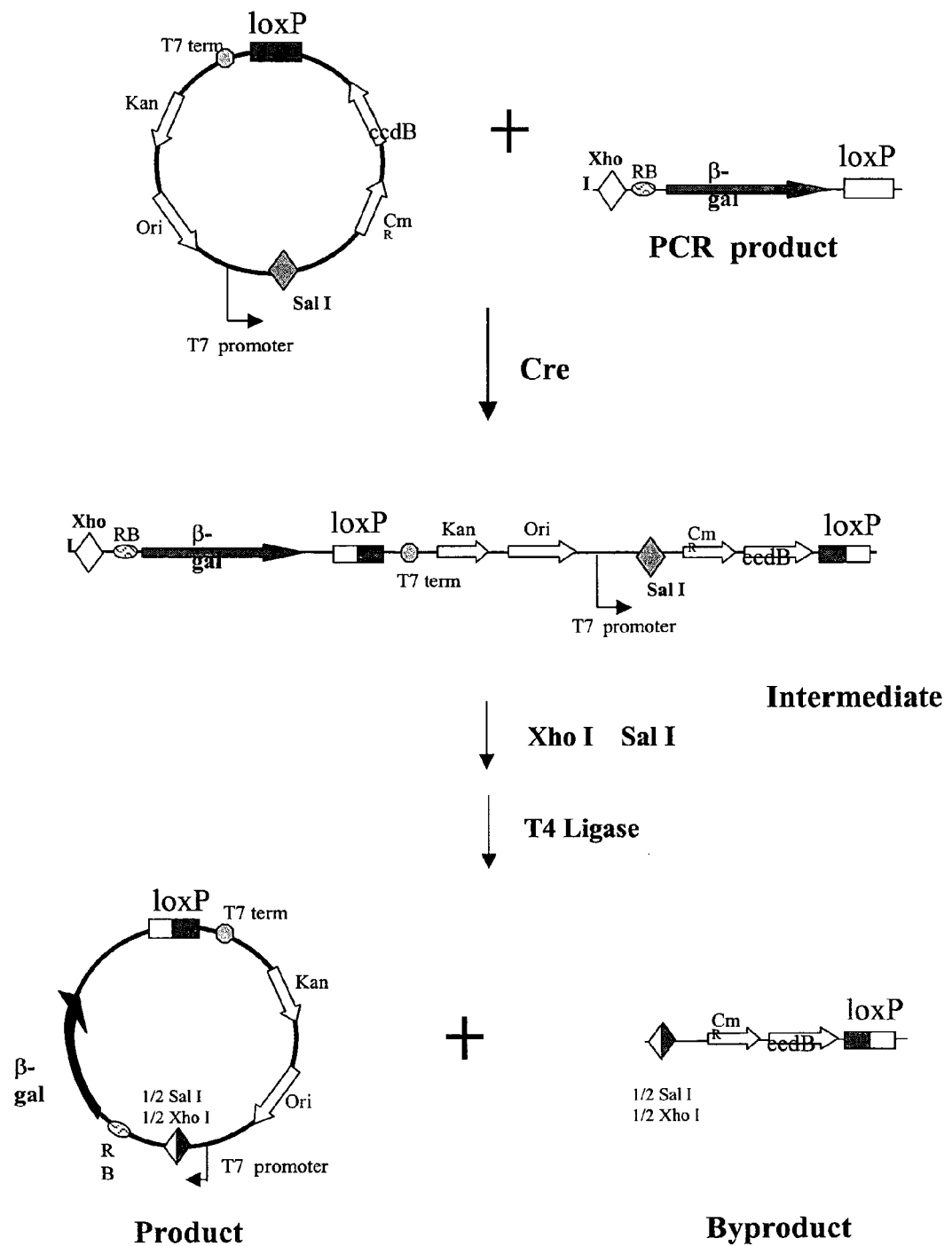

FIG. 17 is yet another example of the method shown in FIG. 1a, where the coding sequence is β-galactosidase gene (β-gal), and the recombination system is loxP-Cre.

FIG. 18 is a schematic depiction of a nested PCR method using PCR primers comprising the linker sequences of the invention.

FIG. 19 is a schematic depiction of pDeliver001 and pDeliver002.

FIG. 20 is a schematic depiction of pDeliver001x and pDeliver002x.

FIG. 21 is a schematic depiction of pDeliver005 and pDeliver006.

FIG. 22 is a schematic depiction of pReceiver003 and pReceiver004.

FIG. 23 is a schematic depiction of pReceiver005 and pReceiver006.

Figure 24:
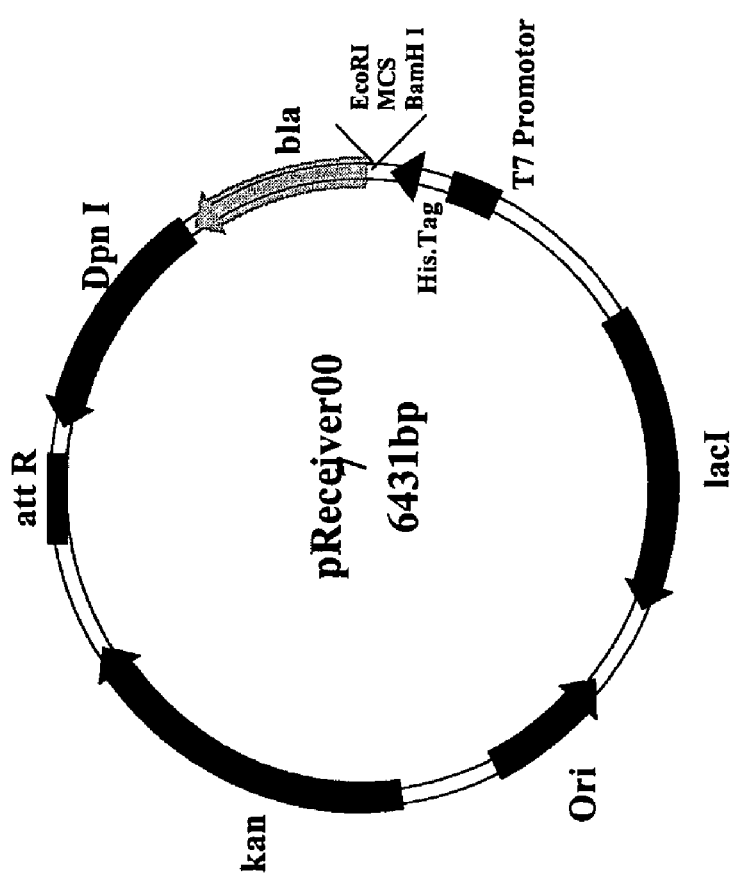

FIG. 24 is a schematic depiction of pReceiver007.

FIG. 25 is a schematic depiction of pDeliver008, pDeliver008x, and pDeliver008y and details of their respective multiple cloning site (MCS) (SEQ ID NO: 25, SEQ ID NO: 26, and SEQ ID NO: 27, respectively), promoter and linker sequences.

Figure 26:
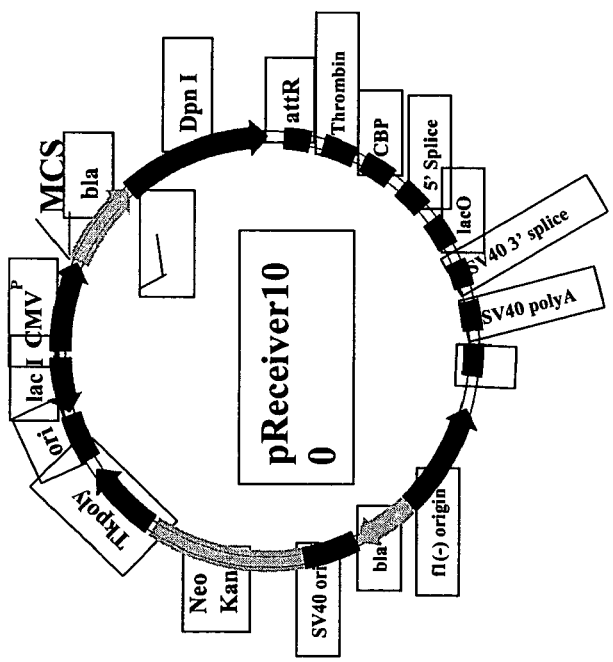

FIG. 26 is a schematic depiction of pReceiver100 and pReceiverx and their respective MCS (SEQ ID NO: 28 and SEQ ID NO: 29).

DETAILED DESCRIPTION OF THE INVENTION

The present invention is now described in detail with references to the drawings. FIG. 1 depicts one general embodiment of a method according to the present invention, wherein the two starting DNA molecules ("Parent Molecules" hereinafter) may be circular or linear. For description purposes, the two Parent Molecules are designated Delivering Molecule and Receiving Molecule, respectively.

Delivering Molecule comprises two segments, A and B. If Delivering Molecule is circular, A and B are separated by a site-specific recombination site, RS1, and a first region ("joinable end site" or "cleavage site") ("CS1") that can be converted into at least a first joinable end ("JE1"). If Delivering Molecule is linear, then A and B are separated by RS1, and one of the two ends of the linear molecule is JE1, which is adjacent to A.

Similarly, Receiving Molecule comprises two segments, C and D. If Receiving Molecule is circular, C and D are separated by a site specific recombination site, RS2, and a second region ("CS2") that can be converted into at least a second joinable end ("JE2"). If Receiving Molecule is linear, then C and D are separated by RS2, and one of the two ends of the linear molecule is JE2, which is adjacent to D.

The goal is to transfer a portion of the Delivering Molecule, e.g. Segment A, into Receiving Molecule, replacing a segment on the Receiving Molecule (e.g. Segment C), thereby creating a "Product Molecule" that comprises A and D. For example, A may be a gene or partial gene of any other polynucleotide of interest, and D contains expression signals and/or selection markers and other desired elements, and the Product Molecule so produced is an expression vector.

A site-specific recombinase typically has four activities: (1) recognition of one or two specific DNA sequences; (2) cleavage of the specific DNA sequence or sequences; (3) DNA topoisomerase activity involved in strand exchange; and (4) DNA ligase activity to reseal the cleaved strands of DNA. See Sauer, 1994, Current Opinions in Biotechnology 5:521–527. Conservative site-specific recombination is distinguished from homologous recombination and transposition by a high degree of specificity for both partners. The strand exchange mechanism involves the cleavage and rejoining of specific DNA sequences in the absence of DNA synthesis (Landy, 1989, Ann. Rev. Biochem. 58:913–949).

It is often desirable to select for the Product Molecule AD, and against all other molecules, including the Parent Molecules, the Byproduct(s), and the Intermediate(s).

An ordinarily skilled person in genetic cloning will immediately recognize that Segment D may comprise, in addition to expression signals, drug-resistance marker(s), replication origin(s), expression tags such as His6, GST, and/or specialized elements and recognition sequences for DNA mapping or sequencing, to facilitate the selection and subsequent cloning steps.

One of ordinary skills in cloning will know that numerous selectable markers are easily available. They include but are not limited to DNA segments or polynucleotide or genes that encode products which (1) provide resistance against toxic compounds (e.g., antibiotics); (2) are not otherwise present in the recipient cell (e.g., auxotrophic markers); (3) suppress the activity of a product of another gene; and (4) can be readily identified (e.g., phenotypic markers such as β-galactosidase, fluorescent proteins (such the green fluorescent protein (GFP), cyan fluorescent protein (CFP), and yellow fluorescent protein (YFP)), and cell surface proteins). Selectable markers can be the polynucleotide fragments themselves, including but not limited to antisense nucleotides; DNA fragments that bind products that modify a substrate (e.g. restriction endonucleases); DNA segments that can be used to isolate a desired molecule (e.g. specific protein binding sites); and DNA segments that encode a specific nucleotide sequence which can be otherwise non-functional (e.g., for PCR amplification). The actual process of selection may be by any of many well-known methods, for example, by enrichment, or identification of one or more desired products from a mixture.

Figure 1C:
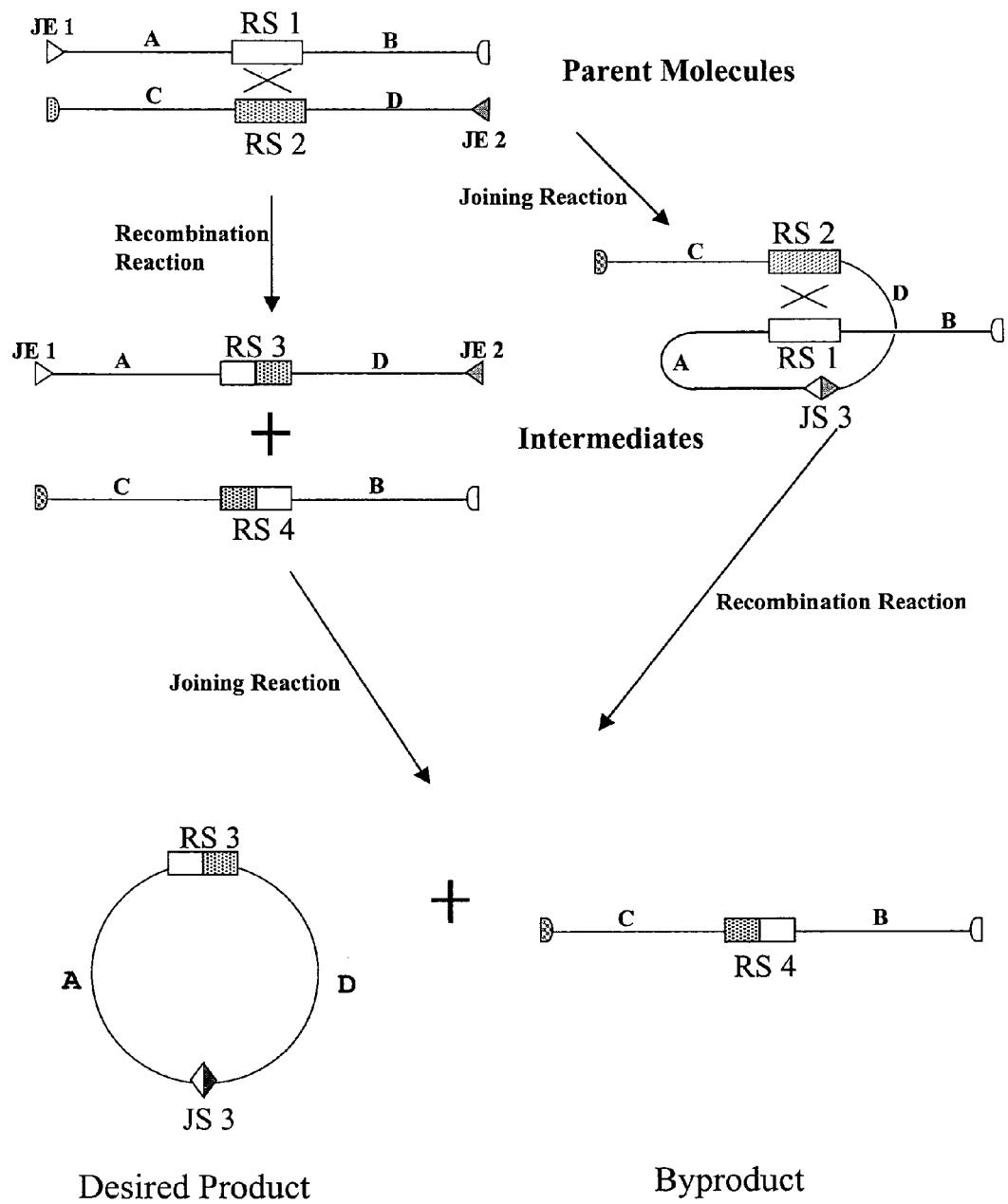
FIG. 1c depicts another embodiment of the present invention wherein both Parent Molecules are linear. Each Parent Molecule comprises a recombiation site and a joinable end. Two pathways are depicted in this Figure. 1) After recombination between the recombination sites (RS1 and RS2), two linear Intermediates are formed. Only one of these two Daughter Intermediates comprises the desired segments A and D, as well as two Joinable Ends, JE1 and JE2. These two joinable ends are finally joined to form a circular Desired Product. 2) After the joining reaction between JE1 of the first Parent Molecule and JE2 of the second Parent Molecule, one linear Intermediate is formed. The recombination between RS1 and RS2 of the Intermediate results in a circular Desired Pruduct with desired segments A and D.
Figure 2:
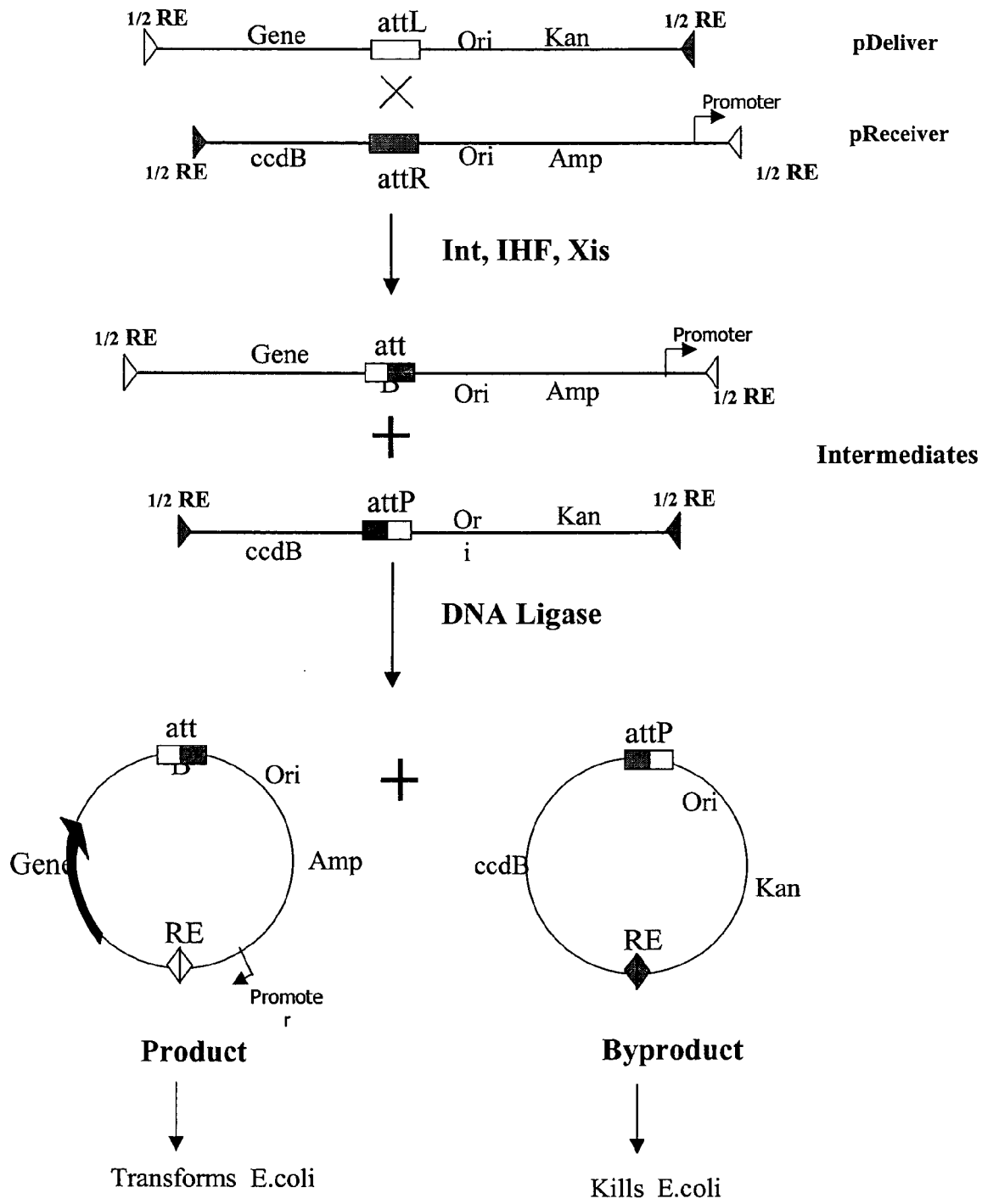
FIG. 2 depicts a specific embodiment of FIG. 1c. First Parent Molecules comprise two joinable ends. By using the recombination sites attL and attR, recombnase proteins Int, IHF, and Xis. Other components of the Parent Molecules are also shown. RE=restriction site, ½ RE=half of a restriction enzyme recognition site, which when joined with another compatible or partner half, forms a complete RE that is recognizable by a suitable restriction endonuclease.
Figure 3:
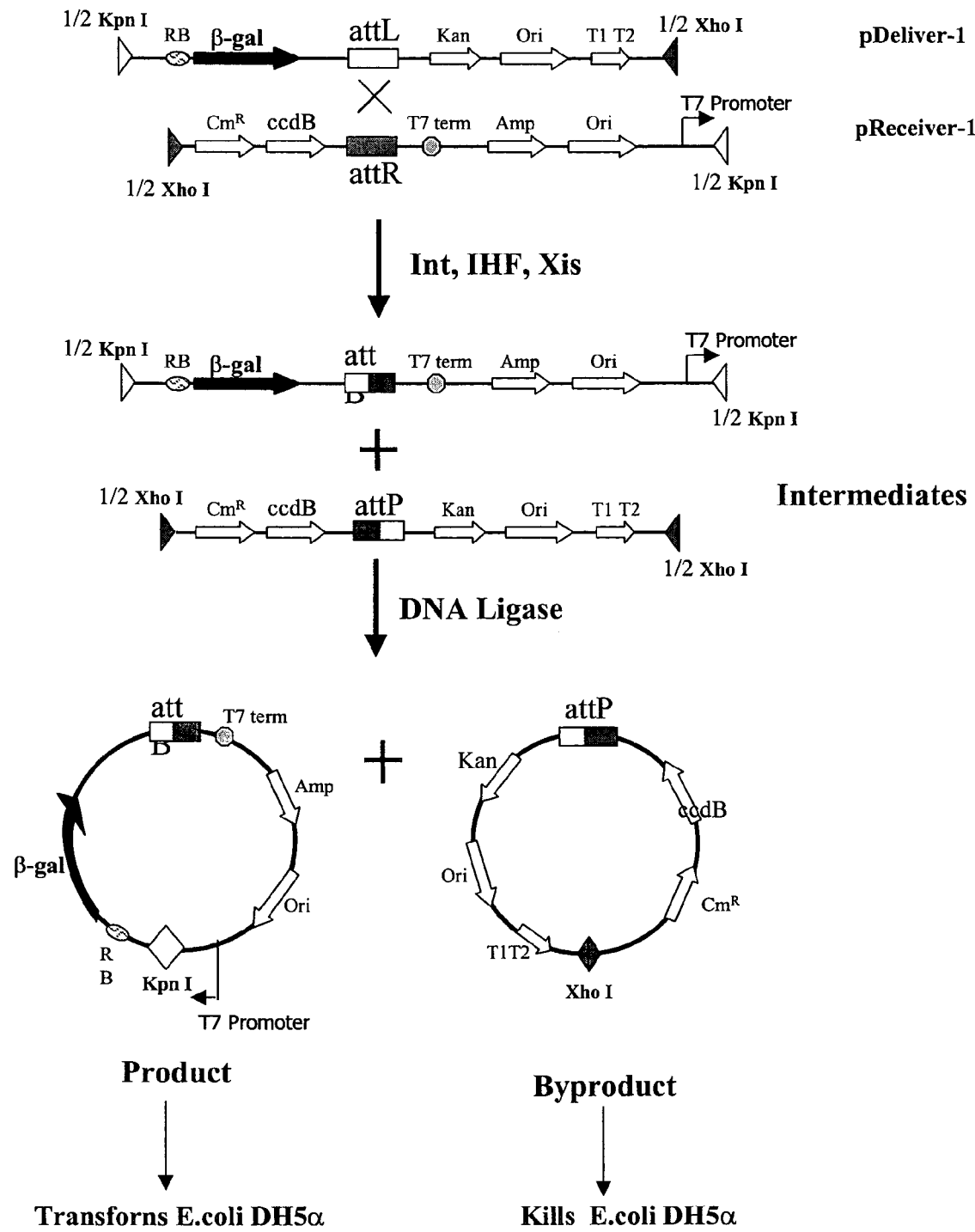
FIG. 3 provides still more details for the embodiment in FIG. 2.
Figure 4:
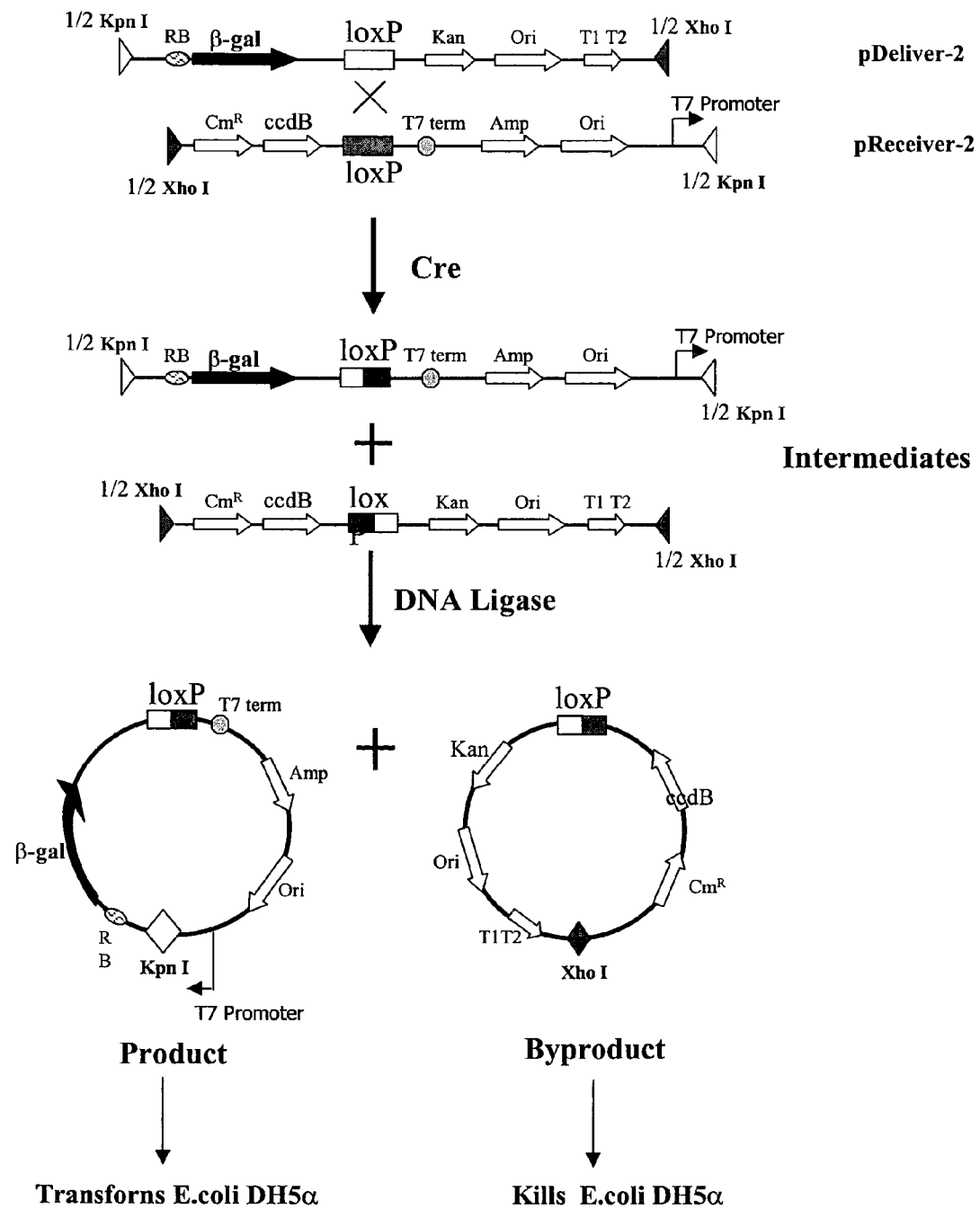
FIG. 4 is an example of FIG. 2 using loxP sites with Cre.

Referring to FIGS. 1a–1c, the above general embodiment will be described in more detail. FIG. 1a depicts the general method in which the Delivering Molecule is circular and the Receiving Molecule is linear. A site-specific recombination reaction produces a linear Intermediate molecule have two ends, one of which ends is JE2. As a result of the recombination reaction, RS1 and RS2 now become RS3 and RS4 (two "product recombination sites"). The Intermediate molecule is cleaved by a cleavage reaction to generate two or more Daughter Intermediates. One Daughter Intermediate comprises segment A and segment D separated by a product recombination site RS3, and its two ends are JE1 and JE2. A final joining reaction circularizes the AD daughter intermediate to form the desired circular Product molecule.

The cleavage and joining reactions may occur in the same reaction mixture, or they may be performed separately. For example, in cases where the joining ends (JEs) are produced by two different restriction enzymes, it is possible for the two JEs to be compatible, yet after they are joined, the newly formed region or site is no longer recognized by either of the two original restriction enzymes, and cannot be cut again. In this case, digestion and ligation may occur in the same reaction tube. FIGS. 14 and 15 and the discussion below exemplifies these situations. Also, if one of the parent molecules is linear and its ends have been treated via dephosphorylation, it will not be able to self-ligate, therefore allowing cleavage and ligation to occur in one step.

The depiction in FIG. 1a also applies to the situation where the Delivering Molecule is linear and the Receiving Molecule is circular.

FIG. 1b depicts the general method of the present invention in which both Parent Molecules are circular. Delivering Molecule comprises A, B, RS1 and CS1, while Receiving Molecule comprises C, D, RS2 and CS2. A recombination reaction generates a circular Intermediate molecule, comprising A, D, C, B, CS1, and CS2 and two product recombination sites RS3 and RS4. Cleavage of the Intermediate molecule at CS1 and CS2 produces Daughter Intermediates AD and CB, with two ends of AD being JE1 and JE2. A joining reaction produces the desired circular Product Molecule AD. The cleavage and joining reactions may occur in the same reaction mixture, or they may be performed separately. The Byproduct molecule CB may be linear or circular.

It will be recognized that if one of the Parent Molecules is cleaved prior to recombination, the method is equivalent to that depicted in FIG. 1a.

FIG. 1c depicts the general method of the present invention in which both Parent Molecules are linear. Delivering Molecule comprises A, B, RS1 and JE1, while Receiving Molecule comprises C, D, RS2 and JE2. In one embodiment, a recombination reaction generates two linear Intermediate molecules, one of which comprises A, D, JE1, JE2, and RS3, which is the product recombination site, while the other of which is a byproduct comprising C, B and RS4. Joining of the Intermediate molecule comprising A and D etc. produces the circular Product Molecule AD. Alternatively, in another embodiment, a joining reaction of the two Parent Molecules produces a linear Intermediate molecule that comprises C, RS2, D, A, RS1 and B. A recombination reaction between RS1 and RS2 produces the desired circular Product Molecule comprising A, D, and RS3. JS3 in this Figure depicts the resulting region when JE1 and JE2 are joined. The cleavage and joining reactions may occur in the same reaction mixture, or they may be performed separately. The Byproduct molecule CB may be linear or circular.

It will be recognized that if both of the circular Parent Molecules depicted in FIG. 1b are cleaved prior to recombination, the method is equivalent to that depicted in FIG. 1c.

As used in the instant disclosure, a "Joinable End" is an end of a DNA molecule that can be linked in vivo or in vitro to a "Partner End" of either the same or different DNA molecules to form a standard 5'-3' phosphodiester covalent bond on one or both strands. In the figures described above, JE1 and JE2 are partner ends.

In one embodiment a joinable end is an end of a double stranded DNA molecule produced by cleavage with a restriction enzyme. A partner end in this case may be the other end produced by the cleavage, or an compatible end produced by cleaving with a different yet "compatible" restriction enzyme(s) that recognize different DNA sequence(s), or otherwise synthesized by one of many method well-known generally in the art.

In another embodiment a joinable end is a DNA end with protruding single stranded 5' or 3' bases of sufficient length to anneal to a partner joinable end with complementary or substantially complementary single stranded bases ("long sticky end").

In another embodiment a joinable end is an end of a double-stranded DNA molecule with a covalently attached protein, that can join to a suitable partner joinable end. For example, a topoisomerase molecule or a molecule with topoisomerase activity, can cleave a specific phosphodiester backbone in one strand, forming a covalent bond between the 3 phosphate of the cleaved strand and a tyrosyl residue of the protein. The phospho-tyrosyl bond between the DNA and the protein can be attacked by a 5' hydroxyl group of another molecule or the other end of the same molecule, releasing the protein and linking the two molecules or the ends of the same molecules. See e.g. Shuman, 1991, Proc. Natl. Acd. Sci. USA 88:10104–10108, and Shuman, 1994, J. Biol. Chem. 269: 32678–32684. Use of topoisomerase, however, may be practically cumbersome. For example, when one or both of the delivering molecules are circular, a linear intermediate molecule may have to be isolated and a topoisomerase molecule attached to one of its end to convert it into a joinable end. Accordingly, a preferred embodiment of the present invention utilizes joinable ends other than an end covalently linked to a topoisomerase.

A preferable joinable end suitable for the present invention is an "irreversible joinable end. By "irreversible joinable end," it is meant that after jointing to another joinable end, the joinable end can not be cut by the same enzyme(s) that is used to create the joinable end. For example, a restriction endonuclease is used to create a first joinable end, and this joinable end is joined with a second joinable end. The region reconstituted by this joining (e.g. ligation) is not recognizable by the restriction enzyme used to create the first joinable end. Using irreversible joinable ends, it is possible for the cleavage and joining reaction to be performed in the same reaction vessel. This further allows the method of the present invention to be performed in a "one-step" fashion, i.e. allowing recombination, cleavage, joining to all occur in one reaction vessel.

It is well known that when an endonuclease digests or cuts a DNA molecule, two ends will be created, and these two ends are compatible and can be ligated back again to reconstitute the original restriction recognition site. Joinable end can be engineered such that it can be hgated back together, but the newly formed site is not recognized by the original neclease used to create the joinable end. For example, one joinable end may be created by SmaI, and the other by XmnI, creating two joinable ends that are compatible but irreversible. When these two ends are ligated, no site is constituted that is recognized by either SmaI or XmnI. There are numerous such pairs of restriction endonucleases known in the art such as GCORI and MfeI. Two blunt ends are also "irreversible joinable ends" according to the present invention.

A "joinable end site" or "cleavage site" or "a region that can be converted into a joinable end" according to the invention is a segment of nucleic acid molecule that can be converted to at least one joinable end. In one embodiment a joinable end site is a recognition site for a restriction enzyme. In another embodiment a joinable end site is a sequence capable of being cleaved, on one or both strands, by a topoisomerase molecule or a molecule with topoisomerase activity.

In a preferred embodiment, the nucleotide sequence of the nucleic acid molecule or fragment of interest in the Delivering Molecule is known, and does not contain any such joinable end site, thereby avoiding an inadvertent cutting or digestion within the nucleic acid molecule or fragment of interest when the cleavage site is converted into a Joinable End.

Site specific recombination proteins perform intra-molecular and inter-molecular site-specific recombinations at two or more specific sites. Site specific recombinases present in some bacteria or viruses have both cleavage and ligation activities, and in some cases along with associated proteins, recognize specific sequences of DNA (recombination sites) and exchange the DNA segments next to or flanked by the recombination site(s).

In a preferred embodiment, recombination sites and recombinases suitable for the instant inventions are, but not limited to, recombination systems of bacteriophage λ (Landy, 1993, supra), bacteriophage P1 (Hoess et al., 1990, In Nucleic Acids and Molecular Biology, vol. 4. Eds.: Eckstein and Lilley, Berlin-Heidelberg: Springer-Verlag; pp. 90–109), and the 2µ circle plasmid of *Saccharomyces cerevisiae* (Broach et al., 1982, Cell 29:227–234). The recombination reaction for these systems (integrase/att sites, Cre/LoxP sites and FLP/FRT sties, respectively) are functional in cell free systems. For example, the integrase/att system or derivatives thereof (listed bellow) could be used in a Delivering Molecule or Receiving Molecule for the recombination catalyzed by Int, IHF and Xis proteins.

The wild-type attB has the following sequence:
AGCCTGCTTTTTTATACTAACTTGA (SEQ ID NO:22)

its corresponding wild type attP sequence is:

AATGCTCTGTTACAGGTCACTAATACCATCTAAGTA (SEQ ID NO: 8)

GTTGATTCATAGTGACTGCATATGTTGTGTTTTACA

GTATTATGTAGTCTGTTTTTTATGCAAAATCTAATT

TAATATATTGATATTTATATCATTTTACGTTTCTCG

TTCAGCTTTTTTATACTAAGTTGGCATTATAAAAAA

GCATTGCTTATCAATTTGTTGCAACGAACAGGTCAC

TATCAGTCAAAATAAAATCATTATTTGATTTC.

The wild type attL sequence is:

AGCCTGCTTTTTTATACTAAGTTGGCATTATAAAAA (SEQ ID NO: 9)

AGCATTGCTTATCAATTTGTTGCAACGAACAGGTCA

CTATCAGTCAAAATAAAATCATTATTTGATTTC, and its corresponding wild type attR is:

AATGCTCTGTTACAGGTCACTAATACCATCTAAG (SEQ ID NO: 10)

TAGTTGATTCATAGTGACTGCATATGTTGTGTTT

TACAGTATTATGTAGTCTGTTTTTTATGCAAAAT

CTAATTTAATATATTGATATTTATATCATTTTAC

GTTTCTCGTTCAGCTTTTTTATACTAACTTGA.

PCR Amplification and Cloning of the Gene of Interest

A large number of expressed genes have been cloned, for example as cDNA clones in cDNA libraries in a few well-known vectors such as pUC, pGem, pBlusscript. Much of these cloned sequences have been sequenced. The most well-known of these large-scale cloning and sequencing effort is the Human Genome Project. Currently, there is a need to subclone these cDNAs or genes of interest into specialized cloning vectors so that the functions of these genes can be analyzed. Subcloning is, however, a very time consuming and expensive effort, and if large scale subcloning is needed for genomics or proteomics research and development efforts, substantial resources will need to be expended.

There are many reasons for subcloning. For example, if the gene of interest, from its sequence information, is believed to be a coding sequence such as a complete open reading frame (ORF), it would be desirable to have the gene expressed and its expression products, in most cases proteins, studied in various organisms or under various conditions. The gene may also need to be manipulated so that some modified products (such as deletion mutants, fusion proteins, and tagged proteins) are produced and studied.

For many subcloning approaches, the gene of interest is first amplified from its source, using PCR or related technologies with primers that contain essentially two portions. The 3' end of the primer is specific to the gene of interest, and is around 20 base pairs long, to ensure that the gene of interest is amplified specifically. The 5' end of the primer usually comprises what is called the linker/adapter sequences. The linker/adapter are additional sequences that facilitate the joining of the amplified fragments with the vector, such as restriction endonuclease recognition sites, and/or specific recombination sites. These sites ensure that the amplified gene of interest can be inserted into the proper part of specialized vectors, in proper orientation and in frame for translation purposes.

In Recombinant DNA molecular cloning, the adapter/linker is often of considerable length, especially when the adapters contain long recombination recognition site. Many of the linkers are over 50 bases long. Such a lengthy adapters/linkers pose two problems. First, it is costly to have to synthesize a primer containing such a lengthy adapter/linker for each gene of interest, especially when a large number of genes need to be screened and tested. More importantly, because most expression vectors contains both the transcription and translation signals for the expression of the gene to be inserted, after insertion of the gene of interest, the actual coding region of the gene would be separated by these adapter/linker sequences. However, as the distance between the start codon (ATG) and the translational signal sequences, such the ribosome binding sites like the Shine-Dalgano sequence (for prokaryotes) and the Kozak Sequence (for eukaryotes), increases, translation efficiency decreases dramatically. As a consequence, the presence of the intervening adapter/linker sequences causes the expression efficiency to be drastically decreased.

Accordingly, in a preferred embodiment, this invention further provides a linker sequence that comprises both restriction endonuclease recognition sites and ribosome binding sites. Specifically, an adapter sequence according to the present invention comprises:
5'-g gaa gga gtt cga acc atg-3' (SEQ ID NO: 1).

A skilled artisan will recognize that SEQ ID NO:1 comprises a specific recognition site for the restriction endonuclease XmnI (i.e. gaaNNNNttc) and a site for NspV (ttcgaa). In addition, SEQ ID NO:1 contains a Shine-Dalgano Sequence (gaaggag), and a Kozak Sequence (ACC) immediately upstream of the start codon (ATG).

When SEQ ID NO:1 is used as part of a primer, additional linker sequences, such as a recognition site for a recombinase or restriction enzyme(s) may be added to its 5' end, and about twenty bases starting from the second codon of the gene or partial gene of interest may be added to the 3'-end of SEQ ID NO: 1. As will be described in more detail below, primers comprising SEQ ID NO: 1 can used to amplify a specific sequence in a conventional PCR, or it can be used in the design of two sets of PCR primers for nested PCR, in which case the SEQ ID NO: 1 will be the primary overlapping region of the two nested primers.

The present invention further provides another adapter having the sequence of
5'-t gcg gcc gca ctc gag cta-3' (SEQ ID NO: 2).

A skilled artisan will recognize that SEQ ID NO:2 comprises a specific recognition site for the restriction endonucleases EagI(cggccg), NotI(gcggccgc) and XhoI (ctcgag). When SEQ ID NO:2 is used as part of a primer, about twenty bases at the 3'-end of the gene, partial gene, or any polynucleotide of interest may be added to the 3'-end of SEQ ID NO: 2.

In one embodiment, the instant invention provides a method for cloning a gene of interest using a first primer and a second primer. The first primer comprises SEQ ID NO: 1 linked a sufficient number of additional nucleotides that are complementary to the sequences of the gene of interest starting from its second codon. The second primer comprises SEQ ID NO: 2 linked to a sufficient number of additional nucleotides that are complementary to the sequences of the gene of interest starting from the last codon. An ordinarily skilled person in the art of performing the polymerase chain reaction will recognize that by "a sufficient number", it is meant that the primers will allow specific amplification of the gene of interest. Generally, this number is between 10–50 bases, preferably, it is between 15–40 bases, more preferably, it is between 18–35 bases, more preferably, it is between 20–30 bases.

In a preferred embodiment, the instant invention further provides a method of nested PCR using the first and second primers described above, and a third and a fourth primers. According to this method, the third PCR primer comprises at its 3'-end a sufficient number of nucleotides that are identical to the 5'-end of the first primer, and at its 5'-end nucleotide sequences that are additional adapter/linker sites. The fourth primer comprises at its 3'-end a sufficient number of nucleotides that are identical to the 5'-end of the second primer, and at its 5'-end nucleotide sequences that are additional adapter/linker sites. The additional linker/adapter sites on the third and fourth primers may be additional restriction endonuclease digestion sites or site-specific recombination sites, or both. These additional sites will allow the final product of the nested PCR reaction to be integrated into another molecule, such as a cloning vector, by way of restriction enzyme cleavage and DNA ligase ligation, or site-specific recombination, or both.

In one embodiment, the gene of interest may be amplified first with the first the second primers. After the completion, or only a few cycles, of this amplification, the amplification products may be further amplified with the third and fourth primers. One skilled in the art will also recognize that all four primers may be added simultaneously and the nested amplification performed without the need to add additional reagents during amplification.

One skilled in the art will immediately recognize that for each given cloning vector, the third and fourth primers are identical, and therefore they can be synthesized in bulk and can be used to clone any gene, if the gene has been amplified by Primers 1 and 2 or other contain ends that complement to the 3'-end of primers 3 and 4. Accordingly, there is only a need to synthesize the first and the second primers for each particular gene of interest. Because unlike in prior methods, the first and the second primers do not need to have the complete adapter/linker sequences, they can be substantially shorter, which will provide substantial cost savings especially in large scale screening efforts.

Additionally, in the cloning vector, the gene of interest will have, immediately upstream of the start codon, a prokaryotic ribosome binding site and/or a eukaryotic ribosome binding site, ensuring that the resultant expression vector can express the gene of interest with high efficiency in both prokaryotic and eukaryotic systems.

Alternatively, SEQ ID NO: 3 may substitute SEQ ID NO: 1 above:

5'-g aag gaa ttc NNN acc atg-3' (SEQ ID NO: 3), wherein NNN can be any three nucleotides other than a stop codon. SEQ ID NO: 3 contains, in addition to the Shine-Dalgano and Kozak sequences, recognition sites for Xmn I (gaaNNNNttc), and EcoR I (gaattc). The triplet NNN allows additional recognition sites to be engineered into the primer and affords the primer even more versatility. For example, when NNN=GGT, a Kpn I site (ggtacc) is created, and when NNN=GCG, An Nru I site is created.

The above linker sequences comprise a specific RBS, i.e. the Shine-Delgano Sequence, and required spacer sequence between the RBS and the start codon of the coding sequence. These linker sequences are incorporated into the nucleic acid fragment of interest and/or a suitable vector. When a vector contains the adapter downstream of a suitable promoter (e.g T7 for $E. coli$ host), a joining reaction of the invention (as described below) will place the fragment of interest in a position such that the start codon ATG is be in suitable distance from the RBS, resulting in an expression vector that can be directly used for transformation and expresses the fragment of interest with high efficiency.

These linker sequences are also suitable for creating an efficient expression vector using recombination cloning method. A recombination site is linked upstream of the adapter, and a vector is provided containing a suitable promoter upstream of a combinable recombination site. By recombination at the 5' end of the gene of interest, an expression vector clone is obtained which can be used to produce native protein in $E. coli$ with only one vector.

In a preferred embodiment, additional adapter/linker sequences for primers 3 and 4 may comprise an att recombination site, for example, the sequence of one strand of the wild-type attB site, AGCCTGCTTTTTTATACTAACTTGAN (SEQ ID NO: 4), or TCAA GTT AGT ATA AAA AAG CAG GCT VN (SEQ ID NO: 23)

wherein N is any one of A, C, T and G and V is any of A, C, G but not T. For example, an oligonucleotide may be a combined SEQ ID NO: 4 and SEQ ID NO: 3, having the sequence of 5'-AGC CTG CTT TTT TAT ACT AAC TTG ANg aag gaa ttc ggt acc atg-3' (SEQ ID NO: 11), or 5'-T CAA GTT AGT ATA AAA AAG CAG GCT VNg aag gaa ttc ggt acc atg-3' (SEQ ID NO: 24)

Or, additional adapter/linker sequences for primers 3 and 4 may be a mutated form of attB, attB1:

GST), the upstream linker sequence will also be translated. In this case, care must be taken to ensure that the joining is in the proper frame that the ATG at the 3' end in SEQ ID NO: 1 is the coding codon for the gene or partial gene of interest. Proper in-frame fusion is important also because the wild type attB sequence contains only one open-reading frame in each strand. In SEQ ID NO: 4 and SEQ ID NO: 23 above, for example, the additional nucleotide N and VN, respectively, is added to ensure the in frame fusion of the SEQ ID NO: 3 in the adapter/linker of SEQ ID NO: 11 and of SEQ ID NO: 24 in the fused product.

The present invention also provides a method for producing an expression vector, without the need for subcloning, using the above PCR primers containing the ribosome biding sites and adapter/linker sequences. This aspect represents an advantageous improvement of the present invention over the current recombination cloning methods in the prior art. Because the amplification products using Primers 3 and 4 above contain adapter/linker sequences, they can be cloned into a receiving vector in which the some or all of the identical sequences of Primers 3 and 4 are present in a proper region, either by way of restriction enzyme digestion followed by ligation, or by way of site-specific recombination, using methods well-known to those of ordinary skills in the art. Because the ribosome binding sites are engineered to be in close proximity to the start codon of the coding sequence, translation efficiency is high, and the vector is also versatile in that it can be used both in prokaryotic and eukaryotic systems.

Referring to FIG. 16, the above one-step expression vector construction method is exemplified using the β-galactosidase gene (β-gal). Using PCR primers described above, a PCR product is produced that comprises β-gal flanked by, at the 5'-end, a suitable ribosome binding site (RB) and a linker sequence comprising an Xho I recognition site, and at the 3'-end, an attB site for the Int and IHF proteins. The receiving vector comprises a restriction site for Sal I, a compatible attP site, and suitably placed promoter (T7), transcription termination signal (T7 term), a replication origin (Ori), and selection markers.

Suitable selection markers include an antibiotic resistance gene and a toxic gene, such as Kan, $Cm^R$, ccdB and Dpn I. These are all well-known in the art and are readily available to one of ordinary skills in the art. See e.g. Bernard, 1996, BioTechniques 21:320–323 (August 1996).

When the PCR product and the receiving vector are incubated together under suitable conditions in the presence of Int and IHF, a site-specific recombination reaction takes

```
5'-GGGG ACA AGT TTG TAC AAA AAA GCA GGC TT-3'   (SEQ ID NO: 5)
or attB2:

5'-GGGG AC CAC TTT GTA CAA GAA AGC TGG GT,      (SEQ ID NO: 6)
or attB1x:

5'-GGGG ACA AGT TTG TAC AAA AAA GCA GGC TT.     (SEQ ID NO: 7)
```

The adapter may also be following partial sequences of wild type recombination sites attP, attL or attR.

Care should be taken so that the placement of the sites should be such that after amplification, the PCR products may be recombed with the cloning vector, and the gene of interest is inserted into the vector in the correct orientation and in the right frame of translation, and that no early translaional termination signal results from the insertion of the gene or partial gene into the vector.

Even though SEQ ID NO: 1 contains the start codon ATG, if it is fused to another gene (such as a tag sequence His6 or place, resulting in a linear intermediate. This linear intermediate is then digested with Xho I and Sal I, and following with ligation with the T4 DNA ligase, a product vector suitable for expression of the β-gal protein in $E. coli$ is produced. Because of the Kan gene on the product vector, clones containing this product vector can be easily selected.

The present invention is now illustrated with examples. It will be understood that the examples below serve to illustrate the inventive methods and compositions and do not limit the present invention in any way.

EXAMPLES

Example 1

Schematic Depictions of Various pDeliver and pReceiver Vecgtors

Various pDeliver and pReceiver vectors are depicted in FIGS. 19–26. FIG. 19 is a schematic depiction of pDeliver001 and pDeliver002. FIG. 20 is a schematic depiction of pDeliver001x and pDeliver002x. FIG. 21 is a schematic depiction of pDeliver005 and pDeliver006. FIG. 22 is a schematic depiction of pReceiver003 and pReceiver004. FIG. 23 is a schematic depiction of pReceiver005 and pReceiver006. FIG. 24 is a schematic depiction of pReceiver007. FIG. 25 is a schematic depiction of pDeliver008 and details of the MCS, promoter and linker sequences. FIG. 26 is a schematic depiction of pReceiver100.

Example 2

Construction of a pDeliver and pReceiver Vector pDeliver Vector

The pDeliver vector in the example comprises:
One recombination site,
a multiple cloning site (MCS) that can be cut by restriction enzyme(s) to produce at lest one joinable end,
two selection marker genes, one encoding a chemical resistant molecule and the other encoding a toxic molecule, and
a replication origin.

If a gene or a partial gene of interest is properly contained in pDeliver, any number of plasmid expression constructs/vectors containing this gene or partial gene of interest can be constructed rapidly. An example of the expression construct is the pReceiver described below.

The restriction enzyme Dpn I recognizes the sequence GATC and cuts that sequence only if the A is methylated by a dam methylase. Expression of Dpn I in dam$^+$ strains of *E. coli*, which is most commonly used in molecular cloning (including the DH5α strain), is lethal because the chromosome of the cell is chopped into many pieces. However, for a dam$^-$ *E. coli* strain, Dpn I is innocuous because the chromosome is immune to Dpn I cutting. Therefore, the gene encoding Dpn I can be used as a negative selection marker.

The plasmid backbone used to generate pDeliver of this example was the pUC19 plasmid. Thus, the origin of replication and the one selectable marker gene of pDeliver were the pUC origin of replication and the pUC Ampicillin resistance gene, respectively. The other selection marker, the gene encoding the Dpn I endonuclease located between the MCS and a recombination site, a wild-type attP of phage λ, were cloned into the backbone. The pUC 19 vector was used, with well-known standard cloning method, to generate pDeliver001 as follows:

pUC19 was digested with EcoR I and Nde I to remove the region containing a partial LacZ gene. Into the remaining fragment was ligated one double-stranded DNA fragments, the bla promoter, that were amplified by PCR with two primers listed below. Before ligation with T4 DNA ligase, the DNA fragment of PCR product were cut with EcoR I and Nde I:

bla Primer (Forward):

5'-GCCGAATTCCCCCTATTTGTTTATTTTTCT-3' (SEQ ID NO: 12)

bla Primer (Reverse):

5'-CCGCATATGCTCTTCCTTTTTCAATATTA-3'. (SEQ ID NO: 13)

The ligated and selected circular plasmid (pUC19-bla) was cut with Eco0109 I and Nde I in order to replace the remaining part of the Lac Z gene by the gene encoding the Dpn I endonuclease such that it is located downstream of the bla promoter. The gene encoding the Dpn I was amplified by PCR using a plasmid containing the Dpn I gene from American Type Culture Collection (ATCC 67494) as a template and the following two primers:

Dpn I Primer (Forward):

5'-ggttgcatatggaattacactttaatttagaa-3' (SEQ ID NO: 14)

Dpn I Primer (Reverse):

5'-aacgagggccttcataatttccgatactttcctc-3'. (SEQ ID NO: 15)

The PCR products was cut with Eco0109 I and Nde I and ligated to pUC119-bla digested with Eco0109 I and Nde I. The ligation reaction was transformed into the dam$^-$ *E. coli* strain SCS110 (Stratagene), producing the plasmid (pUC19-bla-Dpn I).

The pUC19-bla-Dpn I was cut by Aat II and Eco0109 I and ligated to a recombination site, λ attP (wild type), that was amplified by PCR with the phage λ genomic DNA as template and the following two primers, followed by digestion with Aat II and Eco01009 I:

attP Primer (Forward):

5'-GGAAGGCCCTAATGCTCTGTTACAGGTCACT-3' (SEQ ID NO: 16)

attP Primer (Reverse):

5'-GGCGACGTCGAAATCAAATAATGATTTTAT-3'. (SEQ ID NO: 17)

The product of the ligation reaction was transformed into to the dam$^-$ *E. coli* strain SCS110. The resultant plasmid was named pDeliver001.

A skilled artisan will recognize that a similar strategy can be followed to generate other pDeliver Vectors, for example a pDeliver vector that contains a recombination site, a wild-type loxP.

pReceiver Vector

A Receiver molecule is generally used to express gene product, and as such it contains a suitable MCS downstream of a promoter sequence and oriented such as to direct transcription through the MCS. To simply and efficiently transfer a gene or partial gene of interest from Deliver molecule to Receiver molecule with the correct orientation, a sequence-specific recombination site such as an att site of phage λ or a loxP site can be inserted upstream of transcription termination sequence(s) of the Receiver molecule.

Care must be taken to place the MCS in the correct reading frame such that an open reading frame was maintained through the MSC on pReceiver, and the reading frame in the MCS on pReceiver was in-frame with the reading frame found in the corresponding MCS on the pDeliver molecule. This would ensure that the gene or partial gene of interest will be translated in the correct frame. In addition, the sequence comprising the MCS on pReceiver and MCS contained within the donor were designed to avoid the introduction of any in-frame stop codon.

The Receiver molecule may encode a protein domain such as an affinity domain or sequence tag including, but not limited to, glutathione-S-transferase (GST), maltose binding protein (MBP), protein A, protein L, a polyhistidine tract, the c-Myc Tag, the HA tag, the Flag Tag, Green Flourescence protein, etc. These domains facilitate the identification and/or purification of the translation product of the gene or partial gene of interest.

Methods for modification of one expression vector are provided below to illustrate the creation of suitable pReceiver Vector. The pET28a expression vector from Novagen (Madison, Wis.) was cut by Xho I, filled in with the Klenow fragment and then cut with Sal I, followed by the treatment with calf intestinal alkaline phosphatase. The pDeliver002 was cut by Aat II, filled in with the Klenow Fragment, and cut with Sal I to generate the fragment containing the bla promoter-Dpn I gene flanked by MCS at upstream of bla and a loxP at the 3' end of the Dpn I gene, respectively. After ligation with T4 DNA ligase and transformed into the dam⁻E. coli strain SCS110, a Receiver molecule, the pReceiver004 was selected.

By using well-known molecular cloning method and in accordance with the invention, any vector may be used to construct the vectors of the invention. In particular, vectors known in the art and those commercially available can be used to make pDeliver and pReceiver vectors comprise MCS sequence and a site-specific recombination site.

Example 3

In Vitro Gene Cloning with the Cloning System of the Present Invention (Hereinafter the "RecJoin System")

Integrase can be obtained as described by Nash, H. A., Methods of Enzymology 100:210–216 (1983). IHF can be obtained as described by Filutowicz, M., et al., Gene 147: 149–150 (1994).

1) Cloning lacZ Gene Amplified by PCR

DNA fragments amplified by PCR are now routined cloned and studied, especially with wide availability of bioinformatic information and tools that allow the prediction of coding sequences for researchers to design primers with 5' end sequence suitable for desired restriction enzyme(s) that will not cut within the DNA fragment of interest.

The lac Z gene was used to test the cloning method of the invention. The open reading frame of the lac Z gene was amplified by PCR using pGEM® β-Gal (Promega, Madison, Wis.) as template and two primers, the forward primer contains Sma I site at the 5' end and the reverse primer contains a wild-type attB recomination site:

Lac Z Primer (Forward):

5'-AAACCCGGGACCatgttgcagatccatgcacgtaaa-3'  (SEQ ID NO: 18)

Lac Z Primer (Reverse):

5'-GGGGTCAAGTTAGTATAAAAAAGCAGGCTctatttttgacaccagaccaact-3'.  (SEQ ID NO: 19)

The attB site of the phage λ integration system is small (25 bp) and has some sequence flexibility (Nash, H. A. et al., Proc. Natl. Acad. Sci. USA 84:4049–4053 (1987). The wild-type 25 base attB site has one open reading frame for both strands and therefore can be suitable as part of the 5' end of a primer that also comprises the specific sequence of a gene of interest.

The PCR product purified with a commercially available kit (Qiagen) and 100 ng of pReceiver008 were incubated in 20 μl of attB X attP recombination reaction mix (50 mM Tris HCl pH 7.5, 25 mM Tris HCl pH 8.0, 70 mM KCl, 5 mM spermidine, 0.2 mM EDTA, 100 μg/ml BSA, 10% glycerol, Int (40 ng) and IHF (8.0 ng)) for 45 min at 25° C. After heating at 65° C. for 10 min and kept on ice-water for 5 min., 14 μl of the recombination reaction was incubated with 1.0 μl of Pme I (5 unit) and Sma I(5 units), 2.0 μl of 10× digestion buffer at 37° C. for 50 min., followed by addition of 1.0 μl T4 of ligase (20 units) and 1 μl of ATP (20 mM) and incubation at 25° C. for 30 min. 2.0 μl were transformed into E. coli DH5α. After expression, aliquots were spread on LB with top agar plates containing cantamine, x-Gal, IPTG (isopropylthio-β-galactoside) and 60 μg/ml kanamycin and incubated at 37° C. for 18 hours. About 152,000 blue colonies were observed in the plate of RecJoin cloning mix transformation. There was no blue colony in the control plate that contained the same mix without Int, IHF, restriction enzymes and T4 DNA ligase. (note: the number of the colonies were calculated as if the entire transformation reaction (1.0 ml) had been plated, either 2 or 100 μl of the transformation were actually plated.

2) Cloning Firefly Luciferase

The firefly luciferase (Luc) gene was used to test the transferring an ORF from a Deliver molecule to a Receiver molecule of the invention.

a) Cloning Open Reading Frame (ORF) of the Luc Gene into pDeliver Vector

The ORF of Luc gene was amplified by PCR using pGL3-Basic Vector (Promega) as template and two primers, the forward primer containing Sma I and EcoR I and the reverse primer containing a wild-type attB recomination site:

Luc Primer (Forward)

5'-AAGCCCGGGAATTCGGTACC atggaagac gccaaaaacataaa-3'   (SEQ ID NO: 20)

Luc Primer (Reverse):

5'-GGGGT CAA GTT AGT ATA AAA AAG CAG GCTctacacggcgatctt tccgccct-3'.   (SEQ ID NO: 21)

The fragments of PCR product purified with a Qiagen kit and 100 ng of pDeliver001x were incubated in 20 µl of attB X attP recombination reaction mix (50 mM Tris HCl pH 7.5, 25 mM Tris HCl pH 8.0, 70 mM KCl, 5 mM spermidine, 0.2 mM EDTA, 100 µg/ml BSA, 10% glycerol, Int (40 ng) and IHF (8.0 ng)) for 45 min at 25° C. After heating at 65° C. for 10 min and kept on ice-water for 5 min., 14 µl of the recombination reaction was incubated with 1.0 µl of Xmn I (5 unit) and Sma I(5 units), 2.0 µl of 10× digestion buffer at 37° C. for 50 min followed by addition of 1.0 µl T4 of ligase (30 units) and 1 µl of ATP (20 mM) and incubation at 25° C. for 30 min. 2.0 µl were transformed into *E. coli* DH5α, Aliquots were spread on LB agar plates containing 100 µg/ml ampicilline and incubated at 37° C. for 18 hours. Hundreds of colonies were observed on a plate for 50 µl transformation. The plasmind containing the ORF of luc gene (named as pDeliver-luc) was purified with a Qaigen kit. For some experiment, the pDeliver-Luc was linearized with EcoR I restriction enzyme with or without treatment of calf intestinal alkaline phosphatase.

b) Transfer ORF of the Luc Gene to a Mammalian Expression Vector

The pReceiver100x comprising one attR (wild-type) was linearized by cleavage with Mfe I (whose recognition site is within the MCS) and treated with calf intestinal alkaline phosphatase. The linearized pReceiver100x plasmid (100 ng) was mixed with pDeliver-Luc linearized with EcoR I and without treatment with calf intestinal alkaline phosphatase, and incubated in the attL and attR recombination reaction in 20 µl of attL X attR recombination reaction mix (50 mM Tris HCl pH 7.5, 25 mM Tris HCl pH 8.0, 70 mM KCl, 5 mM spermidine, 0.2 mM EDTA, 100 µg/ml BSA, 10% glycerol, Int (40 ng), IHF (8.0 ng) and Xis (4.0 ng) for 45 min at 25° C. After heating at 65° C. for 10 min and kept on ice-water for 5 min. 12.5 µl of the recombination reaction was incubated with 1.0 µl T4 of ligase (30 units), 1.5 µl of 10×T4 ligation buffer and incubation at 25° C. for 30 min. 2.0 µl were transformed into *E. coli* DH5α. Aliquots were spread on LB agar plates containing 60 µg/ml kanamycin and incubated at 37° C. for 18 hours. Hundreds of colonies were observed on a plate for 20 µl transformation. The plasmid containing the ORF of Luc gene was purified by a Qiagen kit for mammalian transfection assay. This plasmid was named as pReceiver100x-Luc).

Example 4

Expression Levels of Luciferase Acitivity

To evaluate the expression level achievable with Rec-Join™ vectors (i.e the Deliver and Receiver vectors), pReceiver100x-Luc plasmid was introduced into mammalian cells (e.g. COS-7 cells) using the geneporter lipofection kit from Gene Therapy Systems). The cells were then cultured for 48 hrs, then harvested and assayed for luciferase activity using a Luciferase Assay System kit from Promega according to the manufacture's instructions. The luciferase activity varied over several orders of magnitude from high level expression to background levels. There results were comparable to those obtained using other commercial available vectors.

All references and patent documents cited herein above are incorporated by reference and should be considered as part of the instant disclosure.

I claim:

1. A method for transferring a nucleic acid fragment of interest from Parent Molecule 1 to Parent Molecule 2 wherein Parent Molecule 1 comprises the nucleic acid fragment of interest and Parent Molecule 2 comprises at least one functional element that is able to influence the transcription, translation or replication of the nucleic acid fragment of interest, or for transferring a nucleic acid fragment of interest from Parent Molecule 2 to Parent Molecule 1 wherein Parent Molecule 2 comprises the nucleic acid fragment of interest and Parent Molecule 1 comprises at least one functional element that is able to influence the transcription, translation or replication of the nucleic acid fragment of interest, wherein Parent Molecule 1 may be linear or circular, and Parent Molecule 2 may be linear or circular;

wherein Parent Molecule 1 comprises a first recombination site and Parent Molecule 2 comprises a second recombination site;

wherein Parent Molecule 1 if linear comprises a first joinable end (JE1), and if circular comprises a first region (CS1) that can be converted into a first joinable end; and wherein Parent Molecule 2 if linear comprises a second joinable (JE2) end and if circular comprises a second region (CS2) that can be converted into a second joinable end;

the method comprising:

(1) mixing Parent Molecule 1 and Parent Molecule 2 in vitro;

(2) forming an intermediate molecule, by either (a) site-specific recombination between the first and second recombination sites, or by (b)(i) joining the first and second joinable ends, or (ii) first converting the region or regions that can be converted into a joinable end or joinable ends, and then joining the joinable ends, the intermediate molecule comprising the nucleic acid molecule of interest and the at least one functional element; and (3) processing the intermediate by either (a) joining the first and the second joinable ends, or (b) by site-specific recombination between the first and second recombination sites, to form a circular Product Vector comprising the nucleic acid molecule of interest and the at least one functional element.

2. The method according to claim 1, wherein Step (3) consists of one recombination reaction between two recombination sites.

3. The method according to claim 1, wherein both Parent Molecules are linear, and the method consists of (1) first joining the two Parent Molecules to form a joined intermediate molecule, and then allowing the joined intermediate molecule to undergo an intramolecular recombination; or (2) first allowing the two Parent Molecules to undergo a recombination to form two linear intermediate molecules and then joining the two joinable ends now on one of the two linear intermediate molecules.

4. The method according to claim 1, wherein at least one of the two Parent Molecules is circular, and the method consists of (1) allowing the two Parent Molecules to undergo site-specific recombination, (2) converting the CS1 or CS2 or both into joinable ends, and (3) joining the joinable ends.

5. The method according to claim 1, wherein at least one of the two Parent Molecules is circular, and the method consists of (1) converting the CS1 or CS2 or both into joinable ends, forming two linear intermediate molecules, (2) allowing the two linear intermediate molecules to undergo site-specific recombination, and (3) joining the joinable ends.

6. The method according to claim 1, wherein at least one of the two Parent Molecules is circular, and the method consists of (1) converting the CS1 or CS2 or both into joinable ends, forming two linear intermediate molecules, (2) joining the joinable ends, and (3) allowing the two linear intermediate molecules to undergo site-specific recombination.

7. A method according to claim 1, wherein all reagents for at least two of the steps (1) the site-specific recombination, (2) converting the region or regions that can be converted into a joinable end or joinable ends, and (3) joining the joinable ends are added to one reaction vessel together.

8. A method according to claim 1, wherein an end of a linear Parent Molecule or an intermediate other than JE1 or JE2 is deactivated and cannot be joined by the joining reaction.

9. A method according to claim 8, wherein an end of a linear Parent Molecule or an intermediate other than JE1 or JE2 is deactivated by dephosphorylation.

10. A method according to claim 1, wherein the functional element comprises at least one member selected from the group consisting of a promoter, a selection marker, a replication origin, a ribosome binding site, a transcription terminator, a coding sequence for a C-terminal tag, a coding sequence for an N-terminal tag, and a protease cleavage site.

11. A method according to claim 1, wherein the joinable end is an end produced by cleavage with at least one restriction enzyme, a blunt end, an end with protruding single stranded 5' or 3' bases of sufficient length to anneal to a partner joinable end with complementary or substantially complementary single stranded bases, or an end comprising a covalently attached protein that can join the end to a suitable partner joinable end.

12. A method according to claim 1, wherein the recombination site is selected from the group consisting of attB (wt), attP(wt), attL(wt), attR(wt), loxP(wt), and frt(wt).

13. A method according to claim 12, wherein the recombination site is selected from the group consisting of attB1, attB2, attB3, attP1, attP2, attP3, attL1, attL2, attL3, attR1, attR2, and attR3.

14. A method of claim 1, further comprising
contacting one or more host cells with the desired circular Product Vector; and
selecting for a host cell comprising said circular Product Vector.

15. A method according to claim 1, wherein in the Product Vector the nucleic acid fragment is downstream of the functional element, and wherein a recombination recognition site is not located downstream of the functional element and upstream of the nucleic acid fragment.

16. A method according to claim 15, wherein the at least one functional element is a translational signal and the nucleic acid fragment encodes a polypeptide.

17. A method according to claim 16, wherein the translational signal and the first translated ATG codon in the product vector are separated by not more than 12 nucleotides.

18. A method according to claim 1, wherein both Parent Molecule 1 and Parent Molecule 2 are linear, wherein Parent Molecule 1 comprises the nucleic acid fragment of interest and Parent Molecule 2 comprising the at least one functional element, and wherein Parent Molecule 1 and Parent Molecule 2 are first incubated in the presence of at least one recombination protein under conditions sufficient to cause recombination of the first and second recombination sites, thereby producing a linear recombination product molecule having two ends and comprising the nucleic acid fragment of interest and the at least one functional element, the two ends of the linear recombination product molecule being the first joinable end and the second joinable end; and the linear recombination product molecule is incubated in the presence of at least one ligation protein under conditions sufficient to cause joining of the first and second joinable ends, thereby producing the circular Product Vector.

19. A method according to claim 1, wherein both the Parent Molecule 1 and Parent Molecule 2 are linear, wherein Parent Molecule 1 comprises the nucleic acid fragment of interest and Parent Molecule 2 comprising at least one functional element, and wherein Parent Molecule 1 and Parent Molecule 2 are first incubated under conditions sufficient to cause joining of the first and second joinable ends, thereby producing a linear joined product comprising the first and second recombination sites, and the nucleic acid fragment of interest and the at least one functional element; and the linear joined product is incubated in the presence of at least one recombination protein under conditions sufficient to cause recombination of the first and second recombination sites, thereby producing a circular Product Vector.

20. A method according to claim 1, wherein Parent Molecule 1 is linear and Parent Molecule 2 is circular, wherein Parent Molecule 1 comprises the nucleic acid fragment of interest and Parent Molecule 2 comprising at least one functional element, and wherein Parent Molecule 1 and Parent Molecule 2 are first incubated in the presence of at least one recombination protein under conditions sufficient to cause recombination of the first and second recombination sites, thereby producing a linear recombination product molecule having two ends, and comprising the nucleic acid fragment of interest and the at least one functional element, and one of the two ends of the linear recombination product molecule being the first joinable end;

the linear recombination product is further incubated in the presence of at least one restriction enzyme under conditions sufficient to cause the region that can be converted into a second joinable end to be converted into the second joinable end, thereby producing a linear digestion product having two ends and comprising the nucleic acid fragment of interest and the at least one functional element, the two ends of the linear recombination product molecule being the first joinable end and the second joinable end, and the linear digestion product molecule is incubated under conditions sufficient to cause joining of the first and second joinable ends, thereby producing the circular Product Vector.

21. A method according to claim 1, wherein Parent Molecule 1 is linear and Parent Molecule 2 is circular, wherein Parent Molecule 1 comprises the nucleic acid fragment of interest and Parent Molecule 2 comprising at least one functional element suitable for the expression of the nucleic acid fragment of interest, and wherein Parent Molecule 2 is first incubated in the presence of at least one restriction enzyme under conditions sufficient to cause the region that can be converted into a second joinable end to be converted into the second joinable end, thereby producing a linear digestion product having a second joinable end, the linear digestion product and Parent Molecule 1 are then incubated under conditions sufficient to cause joining of the first and second joinable ends, thereby producing a linear ligation product comprising the nucleic acid fragment of interest, the at least one functional element and the first and second recombination sites, the linear ligation product is further incubated in the presence of at least one recombination protein under conditions sufficient to cause recombination of the first and second recombination sites, thereby producing the circular product vector.

22. A method according to claim 1, wherein Parent Molecule 1 is circular and comprises the nucleic acid fragment of interest, and Parent Molecule 2 is linear and comprises the second joinable end and at least one functional element, and wherein the first and second vectors are first incubated in the presence of at least one recombination protein under conditions sufficient to cause recombination of the first and second recombination sites, thereby producing a linear recombination product molecule having two ends and comprising the nucleic acid fragment of interest and the at least one functional element, and one of the two ends of the linear recombination product molecule being the second joinable end;

the linear recombination product is further incubated in the presence of at least one restriction enzyme under conditions sufficient to convert the first region into a first joinable end, thereby producing a linear digestion product having two ends and comprising the nucleic acid fragment of interest and the at least one functional element, the two ends of the linear recombination product molecule being the first joinable end and the second joinable end, and the linear digestion product molecule is incubated under conditions sufficient to cause joining of the first and second joinable ends, thereby producing the circular Product Vector.

23. A method according to claim 1, wherein Parent Molecule 1 is linear and Parent Molecule 2 is circular, wherein Parent Molecule 2 comprising the nucleic acid fragment of interest, wherein Parent Molecule 1 comprises at least one functional element, and wherein Parent Molecule 2 is first incubated in the presence of at least one restriction enzyme under conditions sufficient to cause the region that can be converted into a second joinable end, thereby producing a linear digestion product having a second joinable end, the linear digestion product and Parent Molecule 1 are then incubated under conditions sufficient to cause joining of the first and second joinable ends, thereby producing a linear ligation product comprising the nucleic acid fragment of interest, the at least one functional element and the first and second recombination sites, the linear ligation product is further incubated in the presence of at least one recombination protein under conditions sufficient to cause recombination of the first and second recombination sites, thereby producing the circular Product Vector.

24. A method according to claim 1, wherein both Parent Molecule 1 and Parent Molecule 2 are circular, and wherein Parent Molecule 1 and Parent Molecule 2 are first incubated in the presence of at least one recombination protein under conditions sufficient to cause recombination of the first and second recombination sites, thereby producing a circular recombination product molecule comprising the nucleic acid fragment of interest and the at least one functional element, and the first and second regions that can be converted respectively into the first and second joinable ends;

the circular recombination product is further incubated in the presence of at least one restriction enzyme under conditions sufficient to convert the first region into a first joinable end, and the second region into a second joinable end, thereby producing a linear digestion product having two ends and comprising the nucleic acid fragment of interest and the at least one functional element, the two ends of the linear recombination product molecule being the first joinable end and the second joinable end, and the linear digestion product molecule is incubated under conditions sufficient to cause joining of the first and second joinable ends, thereby producing the circular Product Vector.

* * * * *

SEQUENCE LISTING

```
<160> NUMBER OF SEQ ID NOS: 24

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
ggaaggagtt cgaaccatg                                                  19

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
```

```
tgcggccgca ctcgagcta                                            19

<210> SEQ ID NO 3
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (11)..(13)
<223> OTHER INFORMATION: n is a, c, g, or t

<400> SEQUENCE: 3
gaaggaattc nnnaccatg                                            19

<210> SEQ ID NO 4
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (26)..(26)
<223> OTHER INFORMATION: n is a, c, g, or t

<400> SEQUENCE: 4
agcctgcttt tttatactaa cttgan                                    26

<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5
ggggacaagt ttgtacaaaa aagcaggctt                                30

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
ggggaccact ttgtacaaga aagctgggt                                 29

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
ggggacaagt ttgtacaaaa aagcaggctt                                30

<210> SEQ ID NO 8
<211> LENGTH: 248
<212> TYPE: DNA
<213> ORGANISM: Artificial
<220> FEATURE:
<223> OTHER INFORMATION: primer
```

```
<400> SEQUENCE: 8
aatgctctgt tacaggtcac taataccatc taagtagttg attcatagtg actgcatatg    60
ttgtgtttta cagtattatg tagtctgttt tttatgcaaa atctaattta atatattgat   120
atttatatca ttttacgttt ctcgttcagc tttttttatac taagttggca ttataaaaaa   180
gcattgctta tcaatttgtt gcaacgaaca ggtcactatc agtcaaaata aaatcattat   240
ttgatttc                                                           248

<210> SEQ ID NO 9
<211> LENGTH: 105
<212> TYPE: DNA
<213> ORGANISM: Artificial
<220> FEATURE:
<223> OTHER INFORMATION: primer

<400> SEQUENCE: 9
agcctgcttt tttatactaa gttggcatta taaaaagca ttgcttatca atttgttgca    60
acgaacaggt cactatcagt caaaataaaa tcattatttg atttc                  105

<210> SEQ ID NO 10
<211> LENGTH: 168
<212> TYPE: DNA
<213> ORGANISM: Artificial
<220> FEATURE:
<223> OTHER INFORMATION: primer

<400> SEQUENCE: 10
aatgctctgt tacaggtcac taataccatc taagtagttg attcatagtg actgcatatg    60
ttgtgtttta cagtattatg tagtctgttt tttatgcaaa atctaattta atatattgat   120
atttatatca ttttacgttt ctcgttcagc tttttttatac taacttga               168

<210> SEQ ID NO 11
<211> LENGTH: 45
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (26)..(26)
<223> OTHER INFORMATION: n is a, c, g, or t

<400> SEQUENCE: 11
agcctgcttt tttatactaa cttgangaag gaattcggta ccatg                   45

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
gccgaattcc ccctatttgt ttattttttct                                   30

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13
```
ccgcatatgc tcttcctttt tcaatatta                                               29

<210> SEQ ID NO 14
<211> LENGTH: 32
<212> TYPE: DNA
<213> ORGANISM: Artificial
<220> FEATURE:
<223> OTHER INFORMATION: primer

<400> SEQUENCE: 14
ggttgcatat ggaattacac tttaatttag aa                                           32

<210> SEQ ID NO 15
<211> LENGTH: 34
<212> TYPE: DNA
<213> ORGANISM: Artificial
<220> FEATURE:
<223> OTHER INFORMATION: primer

<400> SEQUENCE: 15
aacgagggcc ttcataattt ccgatacttt cctc                                         34

<210> SEQ ID NO 16
<211> LENGTH: 31
<212> TYPE: DNA
<213> ORGANISM: Artificial
<220> FEATURE:
<223> OTHER INFORMATION: primer

<400> SEQUENCE: 16
ggaaggccct aatgctctgt tacaggtcac t                                            31

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
ggcgacgtcg aaatcaaata atgattttat                                              30

<210> SEQ ID NO 18
<211> LENGTH: 36
<212> TYPE: DNA
<213> ORGANISM: Artificial
<220> FEATURE:
<223> OTHER INFORMATION: primer

<400> SEQUENCE: 18
aaacccggga ccatgttgca gatccatgca cgtaaa                                       36

<210> SEQ ID NO 19
<211> LENGTH: 52
<212> TYPE: DNA
<213> ORGANISM: Artificial
<220> FEATURE:
<223> OTHER INFORMATION: primer

<400> SEQUENCE: 19
ggggtcaagt tagtataaaa aagcaggctc tattttgac accagaccaa ct                      52

<210> SEQ ID NO 20
<211> LENGTH: 43
<212> TYPE: DNA

```
<213> ORGANISM: Artificial
<220> FEATURE:
<223> OTHER INFORMATION: primer

<400> SEQUENCE: 20
aagcccggga attcggtacc atggaagacg ccaaaaacat aaa                    43

<210> SEQ ID NO 21
<211> LENGTH: 52
<212> TYPE: DNA
<213> ORGANISM: Artificial
<220> FEATURE:
<223> OTHER INFORMATION: primer

<400> SEQUENCE: 21
ggggtcaagt tagtataaaa aagcaggctc tacacggcga tctttccgcc ct          52

<210> SEQ ID NO 22
<211> LENGTH: 25
<212> TYPE: DNA
<213> ORGANISM: Artificial
<220> FEATURE:
<223> OTHER INFORMATION: primer

<400> SEQUENCE: 22
agcctgcttt tttatactaa cttga                                       25

<210> SEQ ID NO 23
<211> LENGTH: 27
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (27)..(27)
<223> OTHER INFORMATION: n is a, c, g, or t

<400> SEQUENCE: 23
tcaagttagt ataaaaaagc aggctvn                                     27

<210> SEQ ID NO 24
<211> LENGTH: 46
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (27)..(27)
<223> OTHER INFORMATION: n is a, c, g, or t

<400> SEQUENCE: 24
tcaagttagt ataaaaaagc aggctvngaa ggaattcggt accatg                 46
```